(12) United States Patent
Hanson et al.

(10) Patent No.: US 11,963,697 B2
(45) Date of Patent: *Apr. 23, 2024

(54) METHODS, COMPOSITIONS, AND SYSTEMS FOR DEVICE IMPLANTATION

(71) Applicant: The Regents of the University of California, Oakland, CA (US)

(72) Inventors: Timothy L. Hanson, San Francisco, CA (US); Michel M. Maharbiz, El Cerrito, CA (US); Philip N. Sabes, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,978

(22) Filed: Apr. 25, 2023

(65) Prior Publication Data
US 2023/0371981 A1    Nov. 23, 2023

Related U.S. Application Data

(63) Continuation of application No. 15/538,575, filed as application No. PCT/US2015/066879 on Dec. 18, 2015, now Pat. No. 11,660,115.
(Continued)

(51) Int. Cl.
*A61B 17/34*     (2006.01)
*A61B 5/00*      (2006.01)
(Continued)

(52) U.S. Cl.
CPC ........ *A61B 17/3468* (2013.01); *A61B 5/0084* (2013.01); *A61B 5/1473* (2013.01);
(Continued)

(58) Field of Classification Search
CPC ... A61B 5/0476; A61B 5/0478; A61B 5/6846; A61B 5/6847; A61B 5/6848;
(Continued)

(56) References Cited

U.S. PATENT DOCUMENTS 6,175,752 B1    1/2001   Say et al.
6,415,187 B1    7/2002   Kuzma et al.
(Continued)

FOREIGN PATENT DOCUMENTS

WO    2007080595    7/2007

*Primary Examiner* — Ronald Hupczey, Jr.
*Assistant Examiner* — Bradford C. Blaise
(74) *Attorney, Agent, or Firm* — Edward J. Baba; Michael J. Blessent; Bozicevic, Field & Francis LLP

(57) ABSTRACT

Methods, systems, and compositions are provided for implanting an implantable device into a biological tissue (e.g., muscle, brain). A subject implantable device includes: (i) a biocompatible substrate, (ii) a conduit (e.g., an electrode, a waveguide) that is disposed on the biocompatible substrate, and (iii) an engagement feature (e.g., a loop) for reversible engagement with an insertion needle. The biocompatible substrate can be flexible (e.g., can include polyimide). The implantable device is implanted using an insertion needle that includes an engagement feature corresponding to the engagement feature of the implantable device. To implant, an implantable device is reversibly engaged with an insertion needle, the device-loaded insertion needle is inserted into a biological tissue (e.g., to a desired depth), and the insertion needle is retracted, thereby disengaging the implantable device from the insertion needle and allowing the implantable device to remain implanted in the biological tissue.

20 Claims, 23 Drawing Sheets

Related U.S. Application Data

(60) Provisional application No. 62/096,257, filed on Dec. 23, 2014.

(51) Int. Cl.
*A61B 5/1473* (2006.01)
*A61B 5/293* (2021.01)
*A61B 17/00* (2006.01)
*A61N 1/05* (2006.01)
*A61N 5/06* (2006.01)
*A61N 5/067* (2006.01)

(52) U.S. Cl.
CPC .............. *A61B 5/293* (2021.01); *A61B 5/688* (2013.01); *A61B 5/6882* (2013.01); *A61N 1/0531* (2013.01); *A61N 1/0534* (2013.01); *A61N 1/0539* (2013.01); *A61N 5/0601* (2013.01); *A61N 5/0622* (2013.01); *A61B 2017/00526* (2013.01); *A61N 2005/063* (2013.01); *A61N 2005/0651* (2013.01); *A61N 5/067* (2021.08)

(58) Field of Classification Search
CPC ..... A61B 5/6849; A61B 5/685; A61B 5/6867; A61B 5/6868; A61B 5/688; A61B 5/6882; A61B 5/0059; A61B 5/0084; A61B 5/1468; A61B 5/1473; A61B 17/3468; A61N 1/04; A61N 1/05; A61N 1/0529; A61N 1/0531; A61N 1/0534; A61N 1/0536; A61N 1/0539; A61N 5/0601; A61N 5/0622; A61N 2005/063; A61N 2005/0651; A61N 2005/067
See application file for complete search history.

(56) References Cited

U.S. PATENT DOCUMENTS

| | | |
|---|---|---|
| 6,658,302 B1 | 12/2003 | Kuzma et al. |
| 7,343,206 B2 | 3/2008 | Sage et al. |
| 8,543,222 B1 | 9/2013 | Sochor |
| 8,634,932 B1 | 1/2014 | Ye et al. |
| 2007/0060984 A1 | 3/2007 | Webb et al. |
| 2009/0149866 A1 | 6/2009 | Kuzma et al. |
| 2009/0312770 A1 | 12/2009 | Kozai et al. |
| 2010/0114272 A1 | 5/2010 | Haidarliu et al. |
| 2010/0234856 A1 | 9/2010 | Stoianovici et al. |
| 2010/0324644 A1 | 12/2010 | Levi et al. |
| 2011/0172679 A1 | 7/2011 | Kuzma |
| 2011/0319738 A1 | 12/2011 | Woodruff et al. |
| 2014/0025088 A1 | 1/2014 | Zarrouk et al. |
| 2014/0213891 A1 | 7/2014 | Gilgunn et al. |
| 2014/0239600 A1 | 8/2014 | Walsh et al. |
| 2014/0276927 A1 | 9/2014 | Barker et al. |
| 2014/0357983 A1 | 12/2014 | Toomey et al. |
| 2015/0080690 A1 | 3/2015 | Frey et al. |
| 2017/0181707 A1 | 6/2017 | Fries et al. |

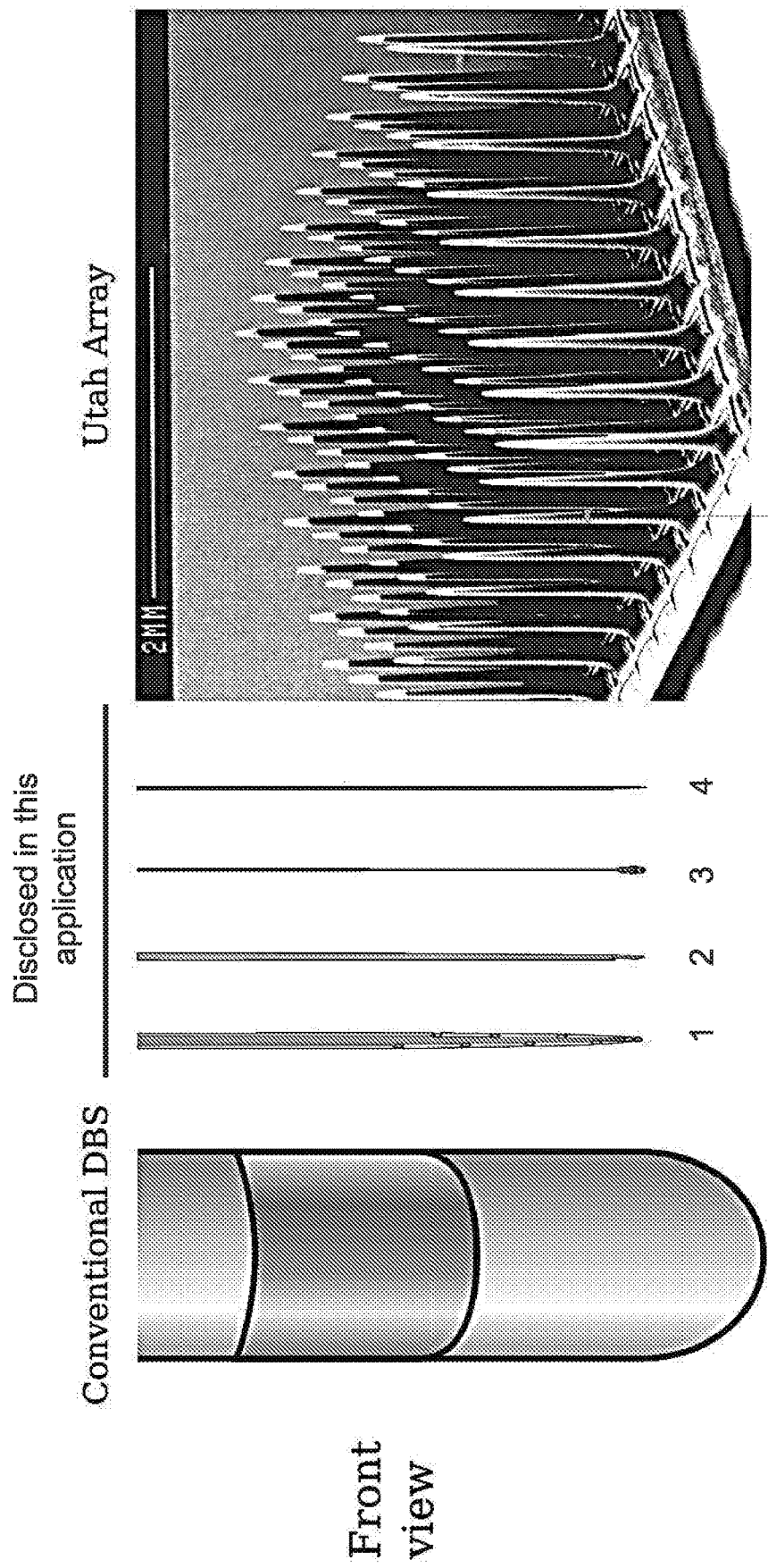

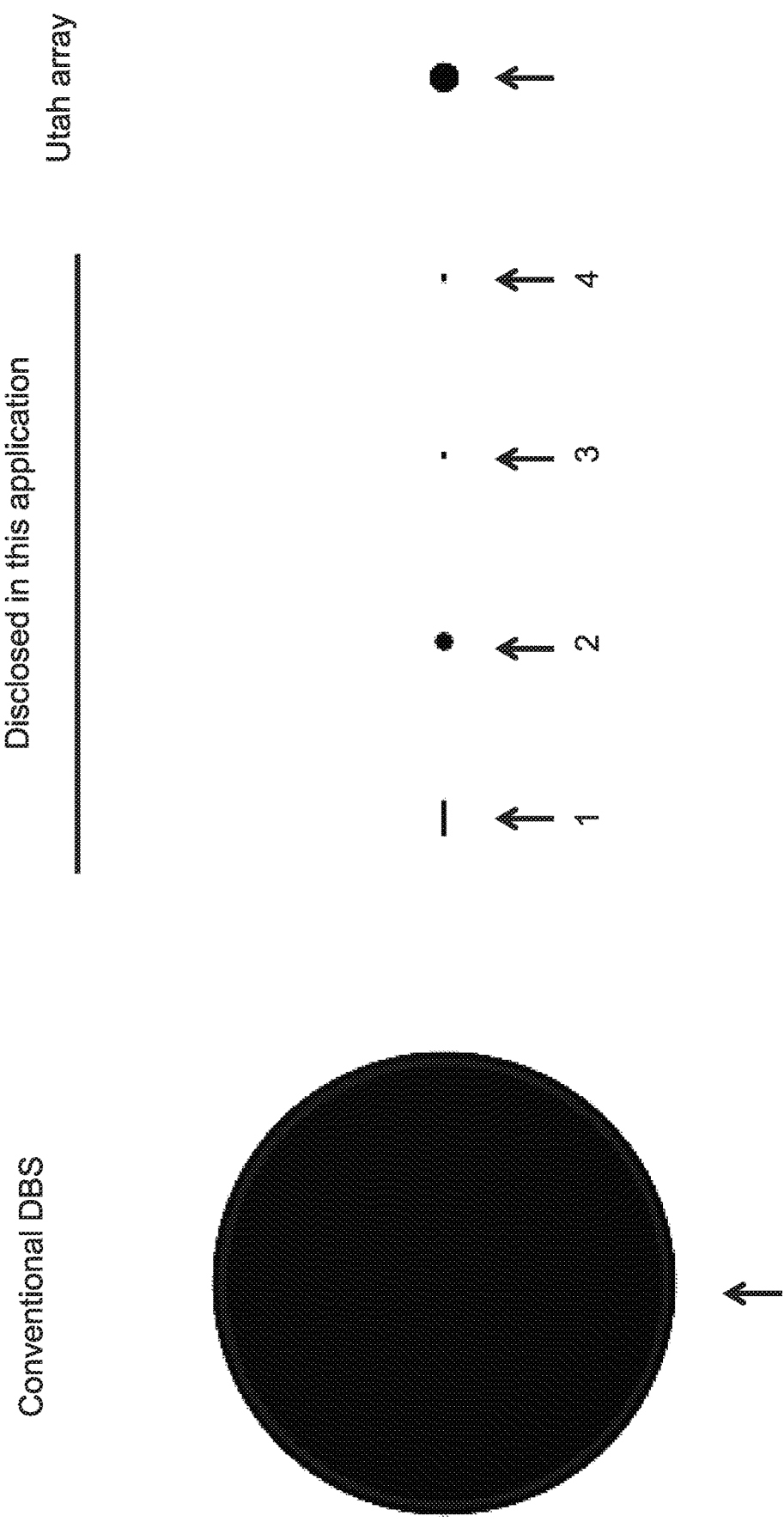
Fig. 2C Relative Size of Cross Sections

10

11

12

13

14 *Evap, pattern Al hardmask*

15

16

10

11 —Evaporate 200nm Al—

13

14

15

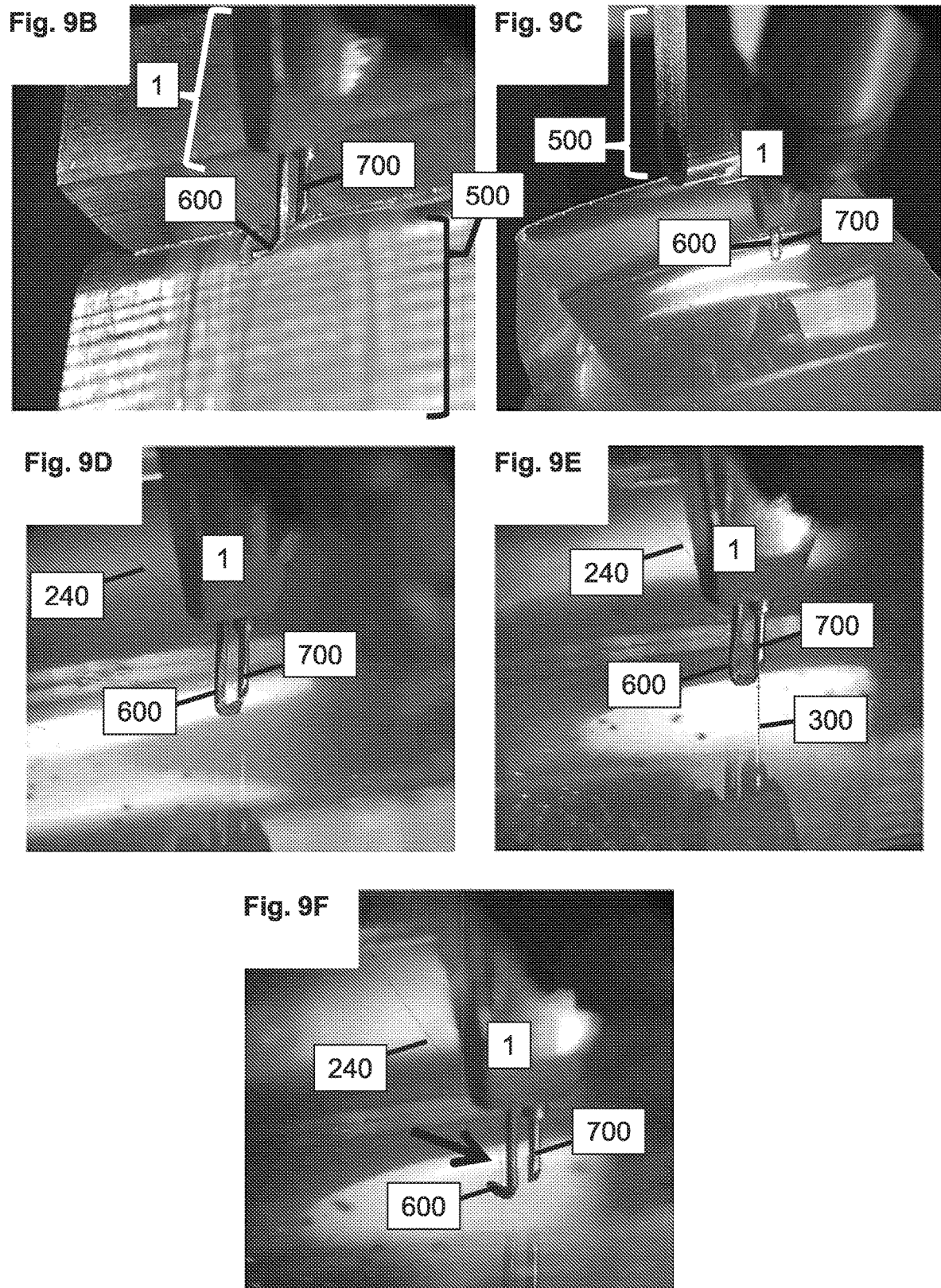

METHODS, COMPOSITIONS, AND SYSTEMS FOR DEVICE IMPLANTATION

CROSS REFERENCE TO RELATED APPLICATIONS

This application is a continuation of U.S. application Ser. No. 15/538,575, filed Jun. 21, 2017, now U.S. Pat. No. 11,660,115, which a U.S. national stage entry of international application PCT/US2015/066879, filed Dec. 18, 2015, which is based upon and claims priority to U.S. provisional patent application 62/096,257, filed Dec. 23, 2014, which applications are incorporated herein by reference in their entirety.

GOVERNMENT SUPPORT

This invention was made with government support under contract no. W911NF-15-2-0054, awarded by Defense Advanced Research Projects Agency. The government has certain rights in the invention.

INTRODUCTION

A fundamental technical barrier to understanding and repairing the brain is the lack of a neural interface with both fine and broad coverage: one that offers access to neural circuits with high spatial and temporal resolution, yet also allows comprehensive access across the brain with long-term stability. For example, prior to this disclosure, there are no current technologies for measuring and manipulating brain activity at both fine (e.g., micron, millisecond) and broad (e.g., centimeter, year) scales.

A conventional approach to large-scale electrode insertion is to combine the electrodes into fixed arrays, such as the Blackrock "Utah" arrays or silicon "Michigan" probes. This approach has many limitations. First, conventional silicon and metal microelectrode arrays are limited in the depth they can achieve, both due to fabrication constraints and the need for rigidity. Second, rigid arrays cannot be optimized to reduce tissue damage and immune response, both because it is not possible to finely adjust the placement of a large fixed array to avoid vascular damage, and because there is a mechanical impedance mismatch between brain tissue and rigid electrodes, resulting in chronic micromotion of the tissue relative to the array, which incites deleterious inflammatory and immune responses. Third, while rigid arrays would seem to allow efficient insertion of a very large number of electrodes, in practice they limit the number that can be inserted in a reasonable surgical time frame. Even with extremely fine needles the brain dimples with insertion pressure, and large arrays can damage the brain by the bed-of-nails effect. This problem is often dealt with by inserting the arrays very slowly, which limits the overall number of electrodes that can be inserted. The opposite approach is employed for the Utah array, where a pneumatic inserter machine implants the array at high speed. Here too there is a substantial time overhead to place and adjust the array for insertion.

Conventional approaches to electrode insertion suffer from limited depth (e.g., probes can only access the first few mm of cortex); limited longevity (e.g., presently neural probes must be stiff to penetrate the brain and evidence suggests that this stiffness along with subsequent mechanical impedance mismatch (the brain is very soft) leads to chronic micromotion, which in turn leads to scarring and loss of recording/stimulating ability); limited targeting (e.g., generally, probes are fabricated in rigid 2D arrays, which cannot be targeted to avoid blood vessels and cannot can be targeted to arbitrary positions throughout the brain); limited due to large size (e.g., evidence supports the idea that the smaller an implant is, the less immune and foreign-body response it elicits—the threshold for being nearly invisible/innocuous is around 6-7 µm); and limited bandwidth (e.g., current technologies can record or modulate only a small fraction of neurons).

There is a need in the art for components, methods, and systems for improved implantation (e.g., implantation with increased efficiency) of conduits (e.g., electrodes, light emitting diodes (LED), waveguides, analyte detectors, etc.) into biological tissues. There is a need in the art for components, methods, and systems for implantation of a plurality of implantable devices (e.g., multiple electrodes) that can be independently implanted (e.g., at any desired location, e.g., depth) within a target tissue (e.g., brain). For example, there is a need in the art for components, methods, and systems that provide for the insertion of an electrode or a plurality of electrodes within a biological tissue with limited tissue displacement, where each electrode is independently inserted and positioned (e.g., at a desired depth within the tissue).

SUMMARY

Methods, systems, and compositions are provided for implanting an implantable device into a biological tissue (e.g., muscle tissue, neural tissue such as a brain, etc.). A subject implantable device includes: (i) a biocompatible substrate (e.g., a flexible biocompatible, inert, non-conductive substrate such as a polyimide-based polymer), (ii) a conduit (e.g., an electrode, a waveguide) that is disposed on the biocompatible substrate, and (iii) an engagement feature (e.g., a loop) for reversible engagement with an insertion needle. The engagement feature of the implantable device can be part of the biocompatible substrate or can be part of the conduit. A subject implantable device is implanted using an insertion needle that includes a corresponding engagement feature to the engagement feature of the implantable device. For implantation, an implantable device is reversibly engaged with an insertion needle (via the corresponding engagement features of the implantable device and the insertion needle), the device-loaded insertion needle is inserted into a biological tissue (e.g., to a desired depth), and the insertion needle is retracted, thereby disengaging the implantable device from the insertion needle and allowing the implantable device to remain implanted in the biological tissue. In some embodiments, a plurality of implantable devices is implanted into the biological tissue using the same insertion needle. For example, in some cases, after the insertion needle engages and implants a first implantable device, the same insertion needle engages and implants a second implantable device (e.g., implants the second implantable device at a different position within the biological tissue than the first implantable device).

Provided are systems that include a subject implantable device and a subject insertion needle (e.g., that include corresponding engagement features). In some cases a subject system includes an insertion device. Also provided are cartridges (implantable device cartridges) that include a plurality of subject implantable devices (e.g., a cartridge can include a flexible backing sheet to which a plurality of implantable devices is adhered), and in some cases, a subject system includes such an implantable device cartridge (e.g., in addition to an insertion needle).

Provided is are methods of implanting an implantable device into a biological tissue, and in some embodiments such a method includes: (a) reversibly engaging an engagement feature of an implantable device with a corresponding engagement feature of an insertion needle, thereby generating a device-loaded insertion needle, wherein, in the implantable device comprises: (i) a biocompatible substrate; (ii) a conduit disposed on the biocompatible substrate; and (iii) the engagement feature of the implantable device; (b) inserting the device-loaded insertion needle into a biological tissue to a desired depth within the tissue; and (c) retracting the insertion needle, thereby disengaging the implantable device from the insertion needle and allowing the implantable device to remain implanted in the biological tissue. In some cases, the conduit is a conductor of electrons and is an electrode for stimulating or recording. In some cases, the conduit is a waveguide. In some cases, the implantable device comprises two or more conduits. In some cases, the two or more conduits include two or more electrodes. In some cases, the biocompatible substrate comprises the engagement feature of the implantable device. In some cases, the engagement feature of the implantable device is a loop. In some cases, the distal end of the insertion needle penetrates through the loop during the engaging.

In some cases, the biocompatible substrate of the implantable device is a non-conductive substrate. In some cases, the biocompatible substrate of the implantable device comprises an inert polymeric material. In some cases, the biocompatible substrate of the implantable device comprises polyimide. In some cases, the biocompatible substrate of the implantable device includes one or more anchor arms that flex orthogonal to the body of the implantable device, while remaining connected to the implantable device, as the insertion needle is retracted to facilitate anchoring of the implantable device in the tissue. In some cases, the flex of the one or more anchor arms distorts the engagement feature of the implantable device, thereby facilitating disengagement of the implantable device from the insertion needle. In some cases, the retracting is initiated with a jerk to facilitate disengagement of the implantable device from the insertion needle. In some cases, the retracting is performed with an acceleration of the insertion needle of at least 50,000 meters per second squared (m/s$^2$). In some cases, the insertion needle rotates about its longitudinal axis during the inserting. In some cases, the insertion needle rotates about its longitudinal axis during the retracting. In some cases, the insertion needle rotates in one direction about its longitudinal axis during the inserting, and rotates in the opposite direction about its longitudinal axis during the retracting.

In some cases, the engagement feature of the insertion needle is positioned in a distal region of the insertion needle. In some cases, the engagement feature of the insertion needle is a flange. In some cases, the insertion needle comprises two connected wires and one of the two wires is shorter than the other such that the distal end of the shorter wire forms the flange. In some cases, the insertion needle comprises two wires twisted together forming a helix.

In some cases, the implantable device is a member of a cartridge comprising a plurality of the implantable devices. In some cases, step (a) includes, after the engaging, removing the engaged implantable device from the cartridge. In some cases, the cartridge comprises a flexible backing sheet to which the plurality of implantable devices is adhered. In some cases, the flexible backing sheet comprises parylene. In some cases, step (a) includes, after the engaging, delaminating the engaged implantable device from the flexible backing sheet. In some cases, the method comprises implanting a plurality of implantable devices with the same insertion needle, wherein after the steps (a)-(c) for a first implantable device, the method comprises repeating steps (a)-(c) for one or more additional implantable devices using the same insertion needle. In some cases, the first implantable device and the one or more additional implantable devices are members of a cartridge comprising a plurality of implantable devices, and each time step (a) is performed, one implantable device is removed from the cartridge. In some cases, the insertion needle is guided by micromanipulators. In some cases, the insertion needle is guided by automated micromanipulators controlled by a processor. In some cases, the method results in less than 1.5% tissue displacement.

In some cases, the biological tissue is a brain. In some cases, the brain is a rodent brain, a non-human primate brain, or a human brain. In some cases, the biological tissue is ex vivo. In some cases, the biological tissue is in vivo.

Also provided are systems for implanting an implantable device, and in some cases such a system includes: (a) an implantable device comprising: (i) a biocompatible substrate; (ii) a conduit disposed on the biocompatible substrate; and (iii) an engagement feature configured for reversible engagement with a corresponding engagement feature of an insertion needle; and (b) an insertion needle comprising an engagement feature that corresponds to, and is configured to reversibly engage, the engagement feature of the implantable device. In some cases, the conduit is a conductor of electrons and is an electrode for stimulating or recording. In some cases, the conduit is a waveguide. In some cases, the implantable device comprises two or more conduits. In some cases, the two or more conduits include two or more electrodes. In some cases, the biocompatible substrate comprises the engagement feature of the implantable device. In some cases, the engagement feature of the implantable device is a loop. In some cases, the biocompatible substrate of the implantable device is a non-conductive substrate. In some cases, the biocompatible substrate of the implantable device comprises an inert polymeric material. In some cases, the biocompatible substrate of the implantable device comprises polyimide. In some cases, the biocompatible substrate of the implantable device includes one or more anchor arms configured to flex orthogonal to the body of the implantable device, while remaining connected to the implantable device, in order to facilitate anchoring of the implantable device. In some cases, the one or more anchor arms are configured to flex orthogonal to the body of the implantable device such that the flex distorts the engagement feature of the implantable device.

In some cases, the implantable device is a member of a cartridge comprising a plurality of the implantable devices. In some cases, the cartridge comprises a flexible backing sheet to which the plurality of implantable devices is adhered. In some cases, the flexible backing sheet comprises parylene.

In some cases, the engagement feature of the insertion needle is positioned in a distal region of the insertion needle. In some cases, the engagement feature of the insertion needle is positioned within 100 μm of the distal end of the insertion needle. In some cases, the insertion needle has a maximum cross sectional area of 4000 μm$^2$ or less. In some cases, the insertion needle comprises one or more of: tungsten, tungsten carbide, iridium, a carbon nanotube, boron, a ceramic oxide, and one or more nitrides. In some cases, the insertion needle comprises tungsten. In some cases, the engagement feature of the insertion needle is a flange. In some cases, the insertion needle comprises two connected wires and one of the two wires is shorter than the other such that the distal end of the shorter wire forms the flange. In some cases, the insertion needle comprises two wires twisted together forming a helix. In some cases, the flange is a notch or a ledge. In some cases, the engagement feature of the insertion needle is reversibly engaged with the engagement feature of the implantable device. In some cases, the insertion needle penetrates through the engagement feature of the implantable device. In some cases, the system further comprises a micromanipulator operably connected to the insertion needle. In some cases, the micromanipulator is configured for automated control by a processor.

Also provided are cartridges of implantable devices, and in some cases such a cartridge includes: (a) a plurality of implantable devices that each comprise: (i) a biocompatible substrate; (ii) a conduit disposed on the biocompatible substrate; and (iii) an engagement feature configured for reversible engagement with a corresponding engagement feature of an insertion needle; and (b) a flexible backing sheet to which the plurality of implantable devices is adhered. In some cases, the conduit of at least one implantable device of the plurality of implantable devices is an electrode for stimulating or recording. In some cases, the conduit of at least one implantable device of the plurality of implantable devices is a waveguide. In some cases, the conduit of at least one implantable device of the plurality of implantable devices is a light emitting diode (LED), a laser, or a photodetector. In some cases, at least one implantable device of the plurality of implantable devices comprises two or more conduits. In some cases, at least one implantable device of the plurality of implantable devices comprises two or more electrodes. In some cases, the biocompatible substrate of at least one implantable device of the plurality of implantable devices comprises the engagement feature of the implantable device. In some cases, the engagement feature of at least one implantable device of the plurality of implantable devices is a loop. In some cases, the biocompatible substrate of at least one implantable device of the plurality of implantable devices comprises one or more anchor arms configured to flex orthogonal to the body of the implantable device, while remaining connected to the implantable device, in order to facilitate anchoring of the implantable device. In some cases, the one or more anchor arms are configured to flex orthogonal to the body of the implantable device such that the flex distorts the engagement feature of the implantable device. In some cases, the flexible backing sheet comprises parylene.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 2A-2C depict scale accurate comparisons of disclosed embodiments to conventional electrodes (e.g., for deep brain stimulation).

FIG. 3B is a photograph of such an insertion needle. FIG. 3A and FIG. 3C-3E depict the insertion needle reversibly engaged with an implantable device, forming a device-loaded insertion needle.

FIG. 4A depicts the insertion needle reversibly engaged with an implantable device, forming a device-loaded insertion needle. FIG. 4B is a photograph of an insertion needle that includes a flange formed from a step in the diameter of the insertion needle.

FIG. 5B is a photograph of such an insertion needle. FIG. 5A and FIG. 5C-5D depict the insertion needle reversibly engaged with an implantable device, forming a device-loaded insertion needle.

FIG. 9A-9F are pictures of one embodiment of an implantable device implantation system performing a subject method (e.g., in this case inserting a plurality of implantable devices into agar as a substitute for a biological tissue).

DETAILED DESCRIPTION

Figure 1:
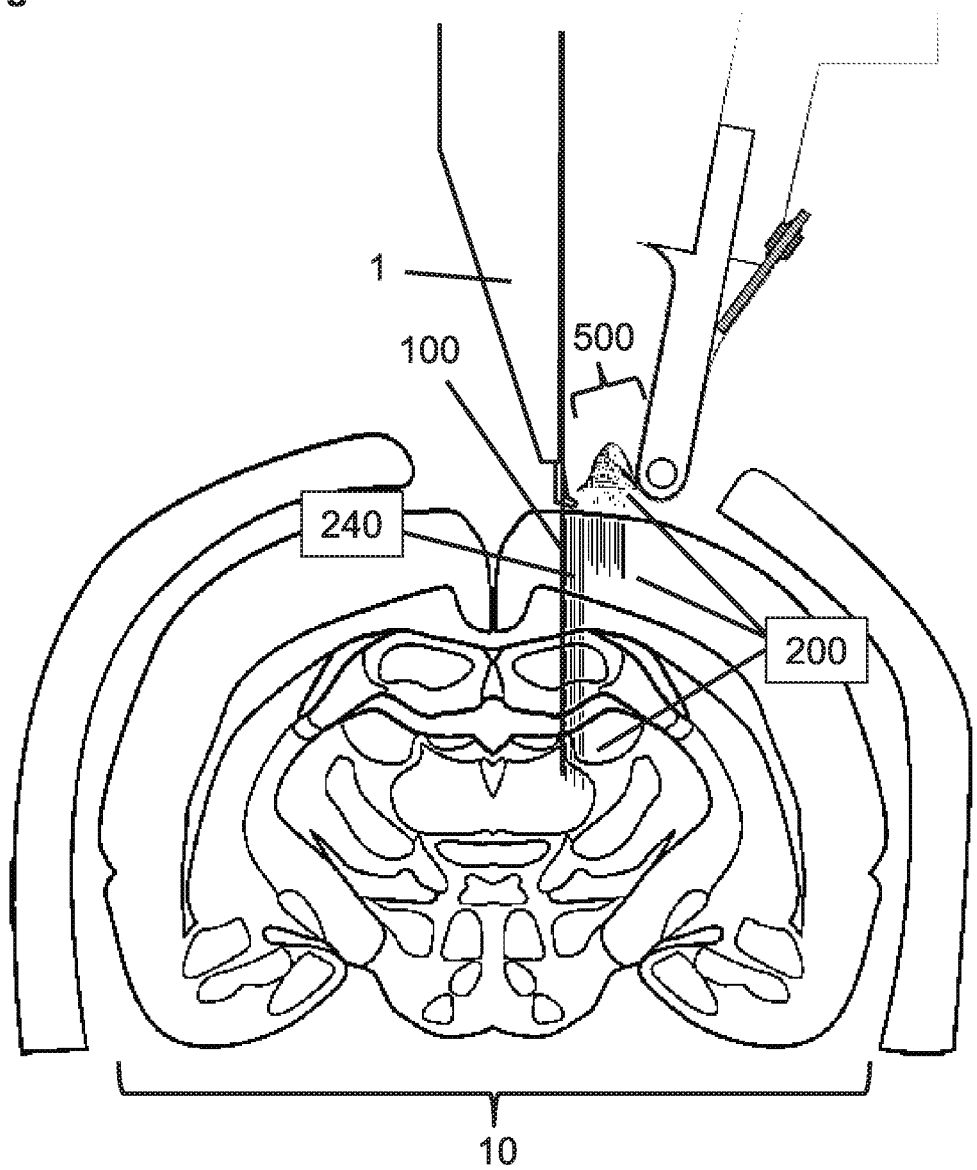
FIG. 1 depicts one embodiment in which a plurality of implantable devices (e.g., each including a conduit such as an electrode) are implanted into a brain.

Methods, systems, and compositions are provided for implanting an implantable device into a biological tissue (e.g., muscle tissue, neural tissue such as a brain, etc.). A subject implantable device includes: (i) a biocompatible substrate (e.g., a non-conductive substrate, e.g., a flexible substrate such as a polyimide-based polymer), (ii) a conduit (e.g., a conductor of electricity such as an electrode, a conductor of photons such as a waveguide) that is disposed on the biocompatible substrate, and (iii) an engagement feature (e.g., a loop) for reversible engagement with an insertion needle.

A subject implantable device is implanted using an insertion needle that includes a corresponding engagement feature to the engagement feature of the implantable device. For implantation, an implantable device is reversibly engaged with an insertion needle (via the corresponding engagement features of the implantable device and the insertion needle), the device-loaded insertion needle is inserted into a biological tissue (e.g., to a desired depth), and the insertion needle is retracted, thereby disengaging the implantable device from the insertion needle and allowing the implantable device to remain implanted in the biological tissue. In some embodiments, a plurality of implantable devices is implanted into the biological tissue using the same insertion needle. For example, in some cases, after the insertion needle engages and implants a first implantable device, the same insertion needle engages and implants a second implantable device (e.g., implants the second implantable device at a different position within the biological tissue than the first implantable device).

Provided are systems that include a subject implantable device and a subject insertion needle (e.g., that include corresponding engagement features). In some cases a subject system includes an insertion device. Also provided are cartridges that include a plurality of subject implantable devices (e.g., a cartridge that includes a flexible backing sheet to which a plurality of implantable devices is adhered).

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

It must be noted that as used herein and in the appended claims, the singular forms "a", "an", and "the" include plural referents unless the context clearly dictates otherwise. Thus, for example, reference to "a needle" includes a plurality of such needles and reference to "the implantable device" includes reference to one or more implantable devices and equivalents thereof, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, Components, and Systems

Provided are methods, components, and systems for implanting an implantable device into a biological tissue (e.g., muscle tissue, brain tissue, etc.) using an insertion needle.

Implantable Device

A subject implantable device includes: (i) a biocompatible substrate (e.g., a non-conductive substrate, e.g., a flexible substrate such as a polyimide-based polymer), (ii) a conduit (e.g., a conductor of electricity such as an electrode, a conductor of photons such as a waveguide) that is disposed on the biocompatible substrate, and (iii) an engagement feature (e.g., a loop) for reversible engagement with an insertion needle. In some cases, the biocompatible substrate includes the engagement feature of the implantable device. In some cases, the conduit includes the engagement feature of the implantable device. A subject insertion needle includes an engagement feature that corresponds to the engagement feature of the implantable device.

As used herein the term "conduit" refers to a substance that can conduct information to an external device. A conduit can be a conductor of electricity (e.g., an electrode), a conductor of photons (e.g., a waveguide such as an optic fiber), a conductor of fluid (e.g., a microfluidic channel), etc. As such, a subject implantable device can be used for a large variety of purposes, and this will depend on the nature of the conduit(s) present as part of the implantable device. For example, an implantable device can be used as (1) a sensor (detector), (2) an effector (e.g., to deliver a stimulation such as light, current, and/or a drug, e.g., which can change the tissue environment into which the device is implanted), or (3) both, depending on the nature of the conduit(s) present as part of the implantable device.

Examples of when a subject implantable device can be used as a sensor include, but are not limited to situations in which the device includes, as a conduit: (i) an electrode that is used as a recording electrode; (ii) a chemical sensing element such as an analyte sensor, e.g., a working electrode; (iii) a photodetector, e.g., for radiography and/or in-vivo imaging; etc.

Examples of when a subject implantable device can be used as an effector include, but are not limited to situations in which the device includes, as a conduit: (i) an electrode that is used for stimulation, e.g., for delivering a current; (ii) a light emitting diode (LED) and/or a microscale laser, e.g., for optogenetic applications; and/or (iii) a waveguide (e.g., optical fiber) for delivering light, e.g., for optogenetic applications; etc. In some cases, effectors will effect cells that have been physically, genetically, and/or virally modified to include (e.g., express) biological transducers (e.g., ion channels, RF-sensitive nanoparticles, and the like). For example, a subject implantable device that includes a waveguide (e.g., an optical fiber) may be used to irradiate and effect target naive or transfected tissue.

Because electrodes can be used as sensors (e.g., to detect changes in electrical activity) or as effectors (e.g., to deliver a current to the surrounding tissue), an implantable device that includes an conductor (e.g., an electrode) as a conduit can function in some cases as a sensor, as an effector, or as both. For example, electrodes can be used for closed and/or open-loop micro or macro stimulation.

As used herein the phrase "disposed on" (e.g., when a conduit is disposed on a biocompatible substrate) is meant to encompass cases in which the conduit is present on, within (e.g., sandwiched), or embedded within the biocompatible substrate. In some cases, the biocompatible substrate can provide mechanical shape/structure to the implantable device while the conduit can provide for communication with an external device. For example, a conduit (e.g., an electrode) can be sandwiched between substrate layers (e.g., non-conductive layers) and/or embedded within a biocompatible substrate, and such an element would be considered herein to be "disposed on" the biocompatible substrate (e.g., in some cases the biocompatible substrate can have more than one layer). In some cases, at least a portion of the conduit is exposed to the surrounding environment (e.g., when the conduit is an electrode).

Biocompatible Substrate

The biocompatible substrate can be any convenient biocompatible substrate and in some cases will be an inert and non-conductive (e.g., insulating) biocompatible substrate (e.g., an insulator). In some cases, the biocompatible substrate is flexible (e.g., the biocompatible substrate is a flexible biocompatible substrate, e.g., a flexible biocompatible substrate, e.g., a flexible non-conductive biocompatible substrate). In some cases, the biocompatible substrate is inert. In some cases, the biocompatible substrate is inert and/or non-conductive.

A biocompatible substrate (e.g., a flexible biocompatible substrate) can be made from any convenient material. In some cases a biocompatible substrate (e.g., a flexible biocompatible substrate) comprises an inert polymeric material (e.g., polyimide, e.g., a polyimide-based polymer, parylene, etc.). In some cases a biocompatible substrate (e.g., a flexible biocompatible substrate) comprises polyimide (e.g., comprises a polyimide-based polymer). In some cases, the biocompatible substrate (e.g., a flexible biocompatible substrate) of a subject implantable device includes an inert polymeric material (e.g., polyimide, e.g., a polyimide-based polymer, parylene, etc.). In some cases, the biocompatible substrate of a subject implantable device includes a conductive material such as metal. In some cases, the biocompatible substrate of a subject implantable device includes NiTi (Nickel-Titanium).

For a non-conducting biocompatible substrate, any convenient non-conducting plastic or polymeric material and/or other non-conducting, flexible, deformable material can be used. Examples include but are not limited to thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate). In some cases, a dissolving polymer (e.g. polycaprolactone) can be used as an insertion shuttle. In some cases, a thin layer of dielectric (e.g., ceramic, glass, and the like) can be used as an insulator and barrier layer. In some cases, the first layer can be partially-cured (e.g., partially cured PI), in which case the stack can be PI-dielectric-metal-dielectric (e.g., PI-ceramic-metal-ceramic).

In some cases, a subject implantable device includes one or more insulating and/or moisture barrier layers (e.g., a dielectric, $Al_2O_3$, and the like). In some such cases, such layers might not be ductile (e.g., in some cases such a layer(s) is ductile and in some cases such a layer(s) is not ductile). In some cases, the biocompatible substrate is inert (e.g., can be an inert biocompatible substrate).

In some embodiments, a subject implantable device includes two layers of biocompatible substrate (e.g., non-conductive biocompatible substrate) with metal sandwiched within. In some cases, such an arrangement can provide, e.g., insulation in the inner layer and/or desirable mechanical properties in the outer layer. In some embodiments, a flexible biocompatible substrate of an implantable device includes first and second thin-film (e.g., of polyimide, of parylene, etc.) layers sandwiched around the conduit (e.g., metal). In other words, the conduit (e.g., metal) can be adjacent to the first thin-film (e.g., of polyimide, of parylene, etc.) layer; and the second thin-film (e.g., polyimide or parylene) layer, forming a thin-film metal thin-film sandwich.

Engagement Feature

A subject implantable device includes an engagement feature that can be reversibly engaged by an insertion needle (via a corresponding engagement feature of the insertion needle, e.g., see below). For example, in some cases, the biocompatible substrate of a subject implantable device includes an engagement feature that can be reversibly engaged by an insertion needle (via a corresponding engagement feature of the insertion needle, e.g., see below). In some cases, the conduit of a subject implantable device includes an engagement feature that can be reversibly engaged by an insertion needle (via a corresponding engagement feature of the insertion needle) (e.g., an electrode can be shaped into a loop and serve as both a conduit and the engagement feature of the implantable device).

Figure 3A:
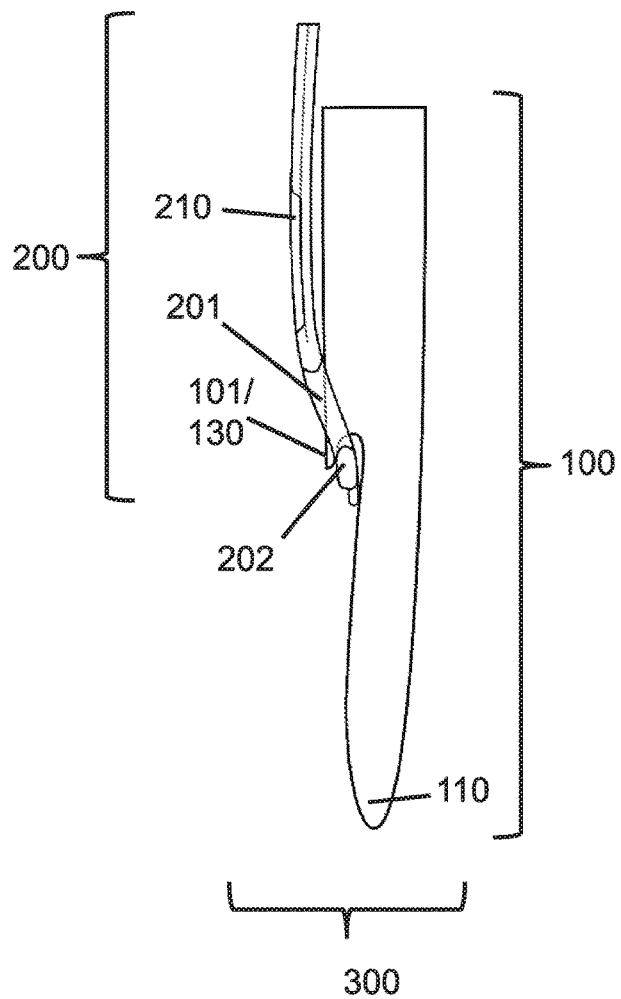
FIG. 3A-3E depict embodiments in which an insertion needle includes an engagement feature that is a flange formed from a notch carved into the body of the insertion needle.

The engagement feature can be any convenient feature that allows for reversible engagement. Examples include, but are not limited to: a loop (a hole in the substrate), a hook, a cup, a protrusion, an extended arm, a "v", etc. In some cases, the engagement feature of a subject implantable device is a loop (a hole). In some cases, the engagement feature of a subject implantable device is fabricated within the biocompatible substrate (e.g., in some cases at or near the end of the implantable device). In some cases, the engagement feature of a subject implantable device is a loop (a hole) fabricated within the biocompatible substrate (e.g., in some cases at or near the end of the implantable device) (e.g., see FIGS. 3A-3E, FIGS. 4A-4B, FIGS. 5A-5D, FIGS. 6A-6C, and FIGS. 7A-7B). In some cases, the engagement feature of a subject implantable device is a loop (a hole) (e.g., in some cases positioned within the biocompatible substrate) having an elongated oval shape so that during insertion, the implantable device can travel on an acute angle to the insertion needle (e.g., see FIG. 3A and FIG. 5A compared to FIG. 4A). In some cases, an engagement feature of a subject implantable device is part of the conduit (e.g., fabricated within the conduit). For example, an engagement feature can be a loop formed from conductive material (e.g., metal) that also functions as an electrode.

Conduit

As noted above, as used herein the term "conduit" refers to a substance that can conduct information to an external device. A conduit can be a conductor of electricity (e.g., an electrode), a conductor of photons (e.g., a waveguide such as an optic fiber), a conductor of fluid (e.g., a microfluidic channel), etc. As such, a subject implantable device can be used for a large variety of purposes, and this will depend on the nature of the conduit(s) present as part of the implantable device. For example, an implantable device can be used as (1) a sensor (detector), (2) an effector (e.g., to deliver a stimulation such as light, current, and/or a drug, e.g., which can change the tissue environment into which the device is implanted), or (3) both, depending on the nature of the conduit(s) present as part of the implantable device.

A subject implantable device includes a conduit. Any convenient conduit can be used and a large variety of conduits are envisioned that would be useful in a large variety of settings, which can depend on context, e.g., what biological tissue is being targeted, what disease or condition is being treated, whether the implanted implantable device(s) will be used for research or therapeutic purposes, etc. Examples of suitable conduits include, but are not limited to: an electrode, a light emitting diode (LED) (e.g., for optogenetic applications), a microscale laser (e.g., for optogenetic applications), a chemical sensing element such as an analyte sensor/detector, a photodetector (e.g., for radiography or in-vivo imaging), an optical element such as a waveguide (e.g., an optical fiber), a reflectometry based sensor, and the like. In some cases, the conduit of a subject implantable device is an electrode. As noted above, in some cases an implantable device that includes an electrode can be used a sensor (detector), an effector (e.g., for stimulation of surrounding tissue), or both.

A conduit (e.g., an electrode for recording and/or stimulation) can comprise (e.g., can be made of) any convenient conductive material. For example, a conduit that conducts electricity (e.g., an electrode) can comprise: copper (Cu), titanium (Ti), copper and titanium, Nickel (Ni), Nickel-Titanium (NiTi, nitinol), chromium (Cr), platinum (Pt), platinum/iridium alloys, tantalum (Ta), niobium (Nb), zirconium (Zr), hafnium (Hf), Co—Cr—Ni alloys, stainless steel, gold (Au), a gold alloy, palladium (Pd), carbon (C), silver (Ag), a noble metal, an allotrope of any of the above, a biocompatible material, and any combination thereof.

In some embodiments, the conduit (e.g., electrode) of a subject implantable device comprises (e.g., is made of) a metalization stack selected from: Cr/Au, SiC/Pt, Pt/SiC, and Ta/Cr/Au. In some cases, the conduit (e.g., electrode) of a subject implantable device comprises Cr/Au (e.g., a Cr/Au metalization stack). In some cases, the conduit (e.g., electrode) of a subject implantable device comprises SiC/Ti/Pt/SiC (e.g., a SiC—Ti—Pt—SiC metalization stack). For example, SiC can be used for adhesion (e.g., as an adhesion layer, e.g., a 5-30 nm thick adhesion layer) to the biocompatible substrate (e.g., in some cases PI), of the subject implantable device while Ti can serve as an adhesion layer (e.g., a 5-30 nm thick adhesion layer) between Pt and SiC).

The conduit can have any convenient cross sectional shape, such as, but not limited to, a circular cross section, a rectangular cross section, a square cross section, a triangular cross section, a planar cross section, or an elliptical cross-section.

In some cases, a subject implantable device includes only one conduit (e.g., an electrode, a wave guide). In some cases, a subject implantable device includes one or more conduits (e.g., electrodes, waveguides) (e.g., two or more, three or more, four or more, five or more, six more, seven or more, eight or more, etc.). In some cases, a subject implantable device includes a plurality of conduits (e.g., electrodes, waveguides) (e.g., 2, 3, 4, 5, 6, 7, 8, 9, 10, 2 or more, 3 or more, 4 or more, 5 or more, 6 more, 7 or more, or 8 or more conduits). In some embodiments, when an implantable device includes more than one conduit (e.g., electrode), each conduit (e.g., electrode, waveguide) can be in communication (e.g., electrical communication, optic communication) with an external device, e.g., can be independently electrically connected to respective wires or fibers (e.g., such that electrical stimulation can be directed to selected electrodes and/or electrical activity can be detected by selected electrodes).

In some cases, a conduit of a subject implantable device is an electrochemical implantable device. An "electrochemical implantable device" is a device configured to detect the presence and/or measure the level of an analyte in a sample via electrochemical oxidation and reduction reactions on the implantable device. These reactions are transduced to an electrical signal that can be correlated to an amount, concentration, or level of an analyte in the sample. For more on using electrodes as an electrochemical implantable device, refer to U.S. Pat. No. 6,175,752, which is hereby incorporated by reference in its entirety.

For example, in some cases, a subject implantable device includes two or more electrodes where one electrode is a working electrode and another electrode is a counter electrode. In some cases, a subject implantable device includes two or more electrodes where one electrode is a working electrode and another electrode is a reference electrode. In some cases, a subject implantable device includes three or more electrodes where one electrode is a working electrode, one electrode is a counter electrode, and one electrode is a reference electrode.

A "counter electrode" refers to an electrode paired with the working electrode, through which passes a current equal in magnitude and opposite in sign to the current passing through the working electrode. The term "counter electrode" is meant to include counter electrodes which also function as reference electrodes (i.e., a counter/reference electrode). A "working electrode" is an electrode at which an analyte (or a second compound whose level depends on the level of the analyte) is electrooxidized or electroreduced with or without the agency of an electron transfer agent. An "electron transfer agent" is a compound that carries electrons between the analyte and the working electrode, either directly, or in cooperation with other electron transfer agents. One example of an electron transfer agent is a redox mediator. "Electrolysis" is the electrooxidation or electroreduction of a compound either directly at an electrode or via one or more electron transfer agents. A "working surface" is that portion of the working electrode which is coated with or is accessible to the electron transfer agent and configured for exposure to an analyte-containing fluid.

Dimensions

A variety of dimensions and geometries are suitable for a subject implantable device and any convenient set of dimensions/geometries can be used, and will likely vary based on various considerations such as, but not limited to: the type of target tissue, the type of conduit present (e.g., electrode, LED, laser, waveguide, etc.), the cost of materials, the rate and/or ease of fabrication, the level of desired tissue displacement, etc.

As used below, the term "maximum diameter" is used in the following context to mean the diameter of the implantable device at the point along its length at which it is its widest, and the term "maximum cross sectional area" is used to mean the cross sectional area of the implantable device at the point along its length at which the cross sectional area is greatest.

In some cases, the implantable device has a maximum diameter of 80 µm or less (e.g., 70µ or less, 65 µm or less, 60 µm or less, 55 µm or less, 50 µm or less, 55 µm or less, 50 µm or less, 45 µm or less, 40 µm or less, 35 µm or less, 30 µm or less, or 25 µm or less). For example, in some cases, the implantable device has a maximum diameter of 65 µm or less. In some cases, the implantable device has a maximum diameter of 35 µm or less.

In some cases, the implantable device has a maximum diameter in a range of from 10 to 80 µm (e.g., from 10 to 70 µm, from 10 to 65 µm, from 10 to 60 µm, from 10 to 55 µm, from 10 to 50 µm, from 10 to 45 µm, from 10 to 40 µm, from 10 to 35 µm, from 15 to 80 µm from 15 to 70 µm, from 15 to 65 µm, from 15 to 60 µm, from 15 to 55 µm, from 15 to 50 µm, from 15 to 45 µm, from 15 to 40 µm, from 15 to 35 µm, from 20 to 80 µm from 20 to 70 µm, from 20 to 65 µm, from 20 to 60 µm, from 20 to 55 µm, from 20 to 50 µm, from 20 to 45 µm, from 20 to 40 µm, from 20 to 35 µm, from 25 to 80 µm from 25 to 70 µm, from 25 to 65 µm, from 25 to 60 µm, from 25 to 55 µm, from 25 to 50 µm, from 25 to 45 µm, from 25 to 40 µm, or from 25 to 35 µm).

In some cases, the implantable device has a maximum diameter in a range of from 20 to 65 µm. In some cases, the implantable device has a maximum diameter in a range of from 25 to 65 µm. In some cases, the implantable device has a maximum diameter in a range of from 20 to 35 µm. In some cases, the implantable device has a maximum diameter in a range of from to 35 µm.

In some cases, the implantable device has a maximum cross sectional area of 5000 $µm^2$ or less (e.g., 4500 $µm^2$ or less, 4000 $µm^2$ or less, 3500 $µm^2$ or less, 3000 $µm^2$ or less, 2500 $µm^2$ or less, 2000 $µm^2$ or less, 1500 $µm^2$ or less, 1000 $µm^2$ or less, 800 $µm^2$ or less, 750 $µm^2$ or less, or 700 $µm^2$ or less). In some cases, the implantable device has a maximum cross sectional area of 4000 $µm^2$ or less (e.g., 3500 $µm^2$ or less, 3000 $µm^2$ or less, 2500 $µm^2$ or less, 2000 $µm^2$ or less, 1500 $µm^2$ or less, 1000 $µm^2$ or less, 800 $µm^2$ or less, 750 $µm^2$ or less, or 700 $µm^2$ or less). In some cases, the implantable device has a maximum cross sectional area of 3500 $µm^2$ or less (e.g., 3000 $µm^2$ or less, 2500 $µm^2$ or less, 2000 $µm^2$ or less, 1500 $µm^2$ or less, 1000 $µm^2$ or less, 800 $µm^2$ or less, 750 $µm^2$ or less, or 700 $µm^2$ or less). In some cases, the implantable device has a maximum cross sectional area of 2000 $µm^2$ or less (e.g., 1500 $µm^2$ or less, 1000 $µm^2$ or less, 800 $µm^2$ or less, 750 $µm^2$ or less, or 700 $µm^2$ or less). In some cases, the implantable device has a maximum cross sectional area of 1000 $µm^2$ or less (e.g., 800 $µm^2$ or less, 750 $µm^2$ or less, or 700 $µm^2$ or less).

In some cases, the implantable device has a maximum cross sectional area in a range of from 250 to 4000 $µm^2$ (e.g., from 250 to 3500 $µm^2$, from 250 to 3000 $µm^2$, from 250 to 2500 $µm^2$, from 250 to 3000 $µm^2$, from 250 to 2500 $µm^2$, from 250 to 2000 $µm^2$, from 250 to 1500 $µm^2$, from 250 to 1000 $µm^2$, from 250 to 800 $µm^2$, from 400 to 4000 $µm^2$, from 400 to 3500 $µm^2$, from 400 to 3000 $µm^2$, from 400 to 2500 $µm^2$, from 400 to 3000 $µm^2$, from 400 to 2500 $µm^2$, from 400 to 2000 $µm^2$, from 400 to 1500 $µm^2$, from 400 to 1000 $µm^2$, from 400 to 800 $µm^2$, from 500 to 4000 $µm^2$, from 500 to 3500 $µm^2$, from 500 to 3000 $µm^2$, from 500 to 2500 $µm^2$, from 500 to 3000 $µm^2$, from 500 to 2500 $µm^2$, from 500 to 2000 $µm^2$, from 500 to 1500 $µm^2$, from 500 to 1000 $µm^2$, from 500 to 800 $µm^2$, from 1000 to 4000 $µm^2$, from 1000 to 3500 $µm^2$, from 1000 to 3000 $µm^2$, from 1000 to 2500 $µm^2$, from 1000 to 3000 $µm^2$, from 1000 to 2500 $µm^2$, from 1000 to 2000 $µm^2$, from 1000 to 1500 $µm^2$, from 2000 to 4000 $µm^2$, from 2000 to 3500 $µm^2$, from 2000 to 3000 $µm^2$, from 2000 to 2500 $µm^2$, from 2000 to 3000 $µm^2$, from 2000 to 2500 $µm^2$, from 2500 to 4000 $µm^2$, from 2500 to 3500 $µm^2$, from 2500 to 3000 $µm^2$, from 2500 to 2500 $µm^2$, or from 2500 to 3000 $µm^2$).

In some cases, the implantable device has a maximum cross sectional area in a range of from 2000 to 4500 $µm^2$. In some cases, the implantable device has a maximum cross sectional area in a range of from 2500 to 4000 $µm^2$. In some cases, the implantable device has a maximum cross sectional area in a range of from 500 to 1000 $µm^2$.

Figure 2A:
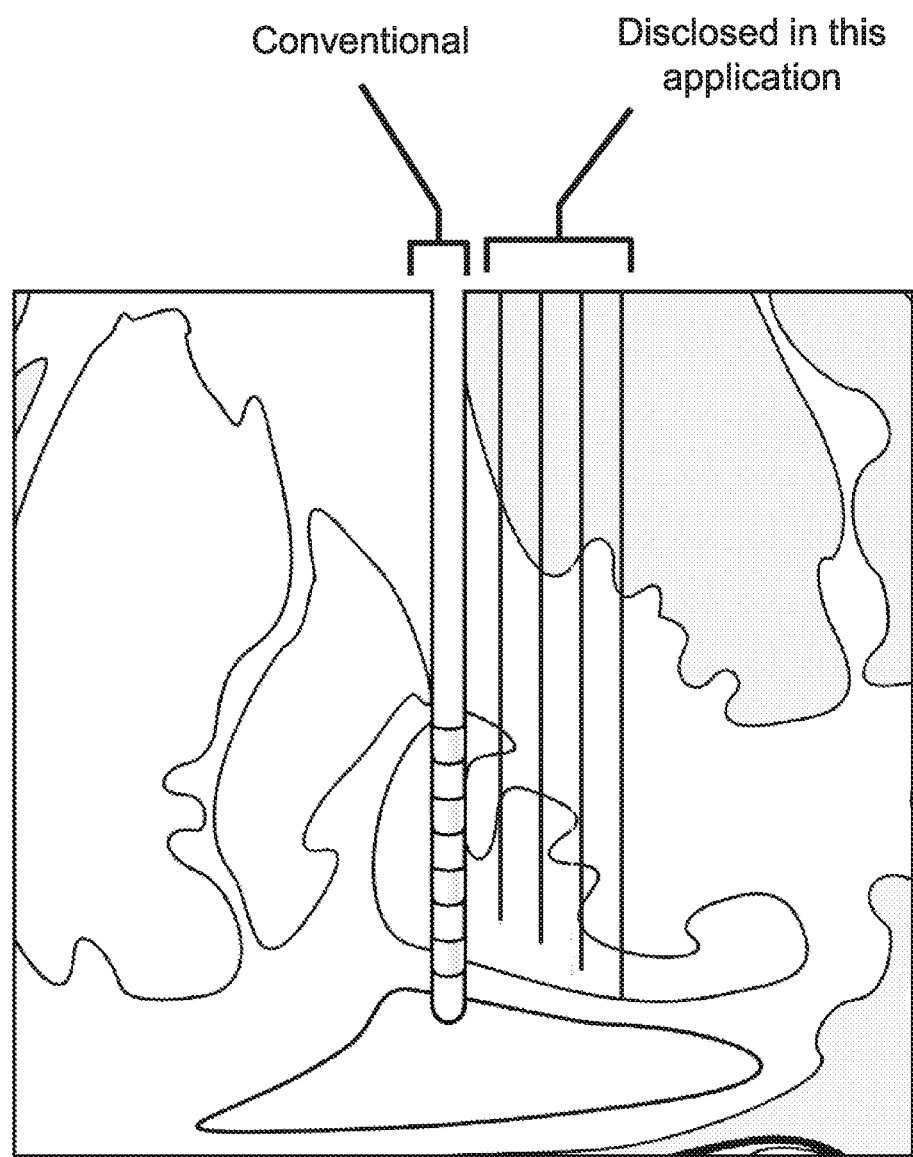

FIG. 2A-2C depict scale-accurate comparisons of disclosed embodiments to conventional electrodes (e.g., conventional electrodes used for deep brain stimulation). As depicted in FIG. 2A, in which four implanted subject implantable devices are shown, in some cases tissue displacement by disclosed implantable devices can be approximately 800 times less than tissue displacement by conventional electrodes. FIG. 2B-2C depicts a scale-accurate comparison of disclosed embodiments to a conventional deep brain stimulation (DBS) electrode and to a conventional "Utah Array." Depicted is a subject implantable device 1 that includes eight conduits (e.g., 8 electrodes), one embodiment of a subject insertion needle 2 that can be used to insert the implantable device 1, a subject implantable device 3 that includes one conduit (e.g., an electrode), and one embodiment of a subject insertion needle 4 that can be used to insert the implantable device 3.

Anchor Arms

In some cases, the biocompatible substrate of a subject implantable device includes one or more anchor arms configured to flex orthogonal to the body of the implantable device, while remaining connected to the implantable device, in order to facilitate anchoring of the implantable device into the targeted biological tissue. This in turn facilitates disengagement of the insertion needle from the implantable device when the insertion needle is retracted. In some cases, one or more anchor arms are configured to flex orthogonal to the body of the implantable device (when the insertion needle is retracted) such that the flex distorts the engagement feature of the implantable device (e.g., changes the shape of the engagement feature), thus facilitating disengagement of the insertion needle from the implantable device.

In some cases, the conduit of a subject implantable device is positioned within (e.g., at the end of) one or more anchor arms. For example, if the conduit is an electrode, the electrode can be positioned in some cases within (e.g., at the end of) the anchor arm.

Figure 7A:
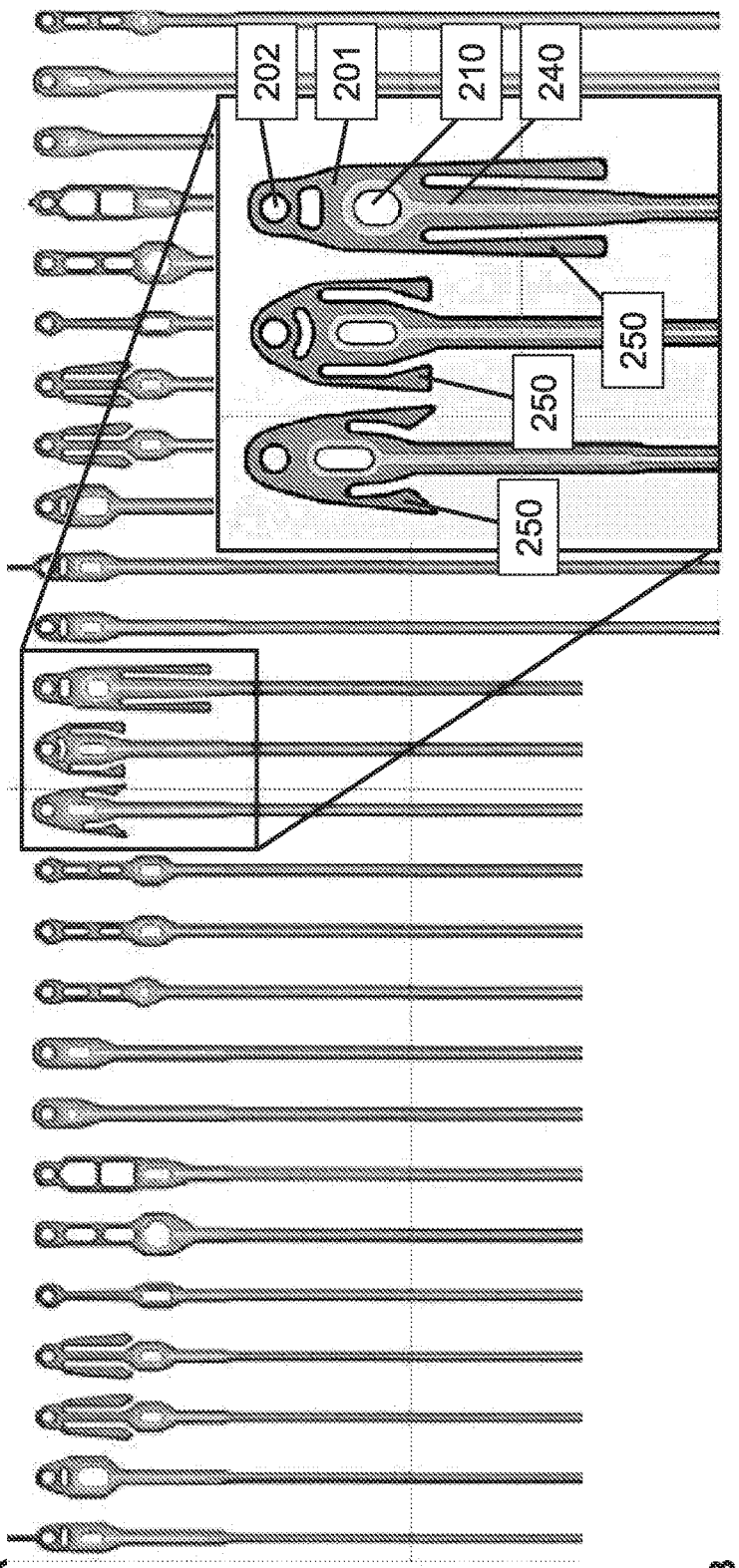
FIG. 7A-7B illustrate a number of different implantable device geometries that were fabricated and tested (all of which were successfully implanted when tested). The inset shows implantable devices that include anchor arms that flex orthogonal to the body of the implantable device, while remaining connected to the implantable device, as the insertion needle is retracted to facilitate (i) anchoring of the implantable device in the tissue, and (ii) disengagement of the implantable device from the insertion needle (e.g., by distorting the engagement feature of the implantable device).
Figure 7B:
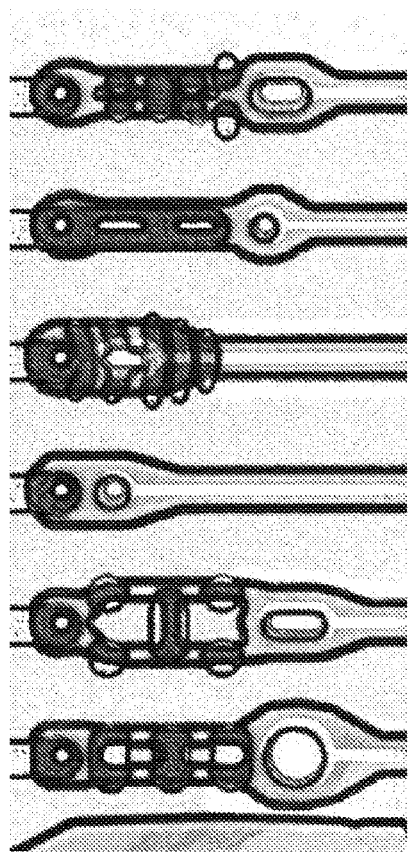

Anchor arms can be any convenient shape and a variety of geometries are envisioned. FIG. 7A-7B illustrate a number of different implantable device geometries that were fabricated and tested. The inset shows implantable devices that include anchor arms 250 that flex orthogonal to the body of the implantable device, while remaining connected to the implantable device, as the insertion needle is retracted to facilitate anchoring of the implantable device in the tissue (e.g., those implantable devices having anchor arms pull out the least with the needle during retraction and disengagement). Thus, the anchor arms 250 served to loosely anchor the implantable device during disengagement/implantation. Flexing of the depicted anchor arms also provided torque to distort (e.g., bend) the engagement feature of the implantable device (e.g., loop) relative to the insertion needle as the insertion needle was retracted. Thus, the anchor arms 250 depicted facilitate disengagement of the implantable device from the insertion needle (e.g., by distorting the engagement feature of the implantable device).

Cartridge of Implantable Devices (Implantable Device Cartridge)

In some cases, a subject implantable device cartridge (i.e., a cartridge that includes a plurality of subject implantable devices) includes a flexible backing sheet (e.g., made from parylene) to which the implantable devices adhere. The term "plurality" as used herein is meant to include a population of more than one. For example two or more is a plurality, e.g., a collection of 2 implantable devices is a plurality of implantable devices as is a collection of 100 implantable devices.

As used herein in the context of implantable devices adhering to a flexible backing sheet of a cartridge, the term "adhere" is used to generally mean that the implantable devices are loosely associated with (loosely adhered to) the flexible backing sheet such that they can be removed from the flexible backing sheet by an engaged insertion needle. Thus, the implantable devices will be adhered to the flexible backing sheet in such a way that they remain associated with the sheet in an organized manor (e.g., with regular spacing forming an array of implantable devices) until an implantable device is engaged with an insertion needle and peeled (delaminated) from the flexible backing sheet. In some cases, an adhesive substance can be used to adhere the implantable devices to the flexible backing sheet. In some cases, the implantable devices adhere to the flexible backing sheet without an adhesive substance (e.g., parylene deposited over polyimide, e.g., a polyimide implantable device, i.e., an implantable device in which the biocompatible substrate comprises polyimide, forms a weak, releasable bond). The flexible backing sheet can be made from any convenient material, e.g., a material that forms a thin film. In some cases, a flexible backing sheet comprises parylene (e.g., a flexible backing sheet can be made of a parylene). In some cases, a flexible backing sheet comprises a parylene-based polymer (e.g., a flexible backing sheet can be made of a parylene-based polymer). In some cases, the flexible backing sheet is a thin film (e.g., a parylene thin-film). Optionally, a flexible backing sheet (e.g., a parylene film) can include one or more dielectric layers to facilitate release of the implantable devices (e.g., implantable devices that include an electrode) from the flexible backing sheet.

In some cases, the flexible backing sheet is bonded (e.g., adhered) to a solid support (e.g., made of stainless steel, e.g., magnetic stainless steel) that permits handling by a machine and/or human.

In some cases, an implantable device cartridge includes break-away tabs such that upon engagement of an implantable device with the insertion needle, the break-away tab is removed (e.g., by snapping/breaking) the tab from the rest of the implantable device. Thus, an implantable device cartridge can include one or more implantable devices that each have a break-away tab (e.g., their biocompatible substrate can include an engagement feature and a break-away tab). For example, see FIG. 3E, which illustrates one possible design for a break-away tab. The size and shape of a break-away tab can be adjusted to work with any desired insertion needle and is not limited to the type of insertion needle depicted in FIG. 3E. In some cases, the break-away tab from one or more implantable devices of the cartridge are interconnected. In some cases, a cartridge includes a flexible backing sheet and one or more implantable devices that each have a break-away tab.

Figure 8A:
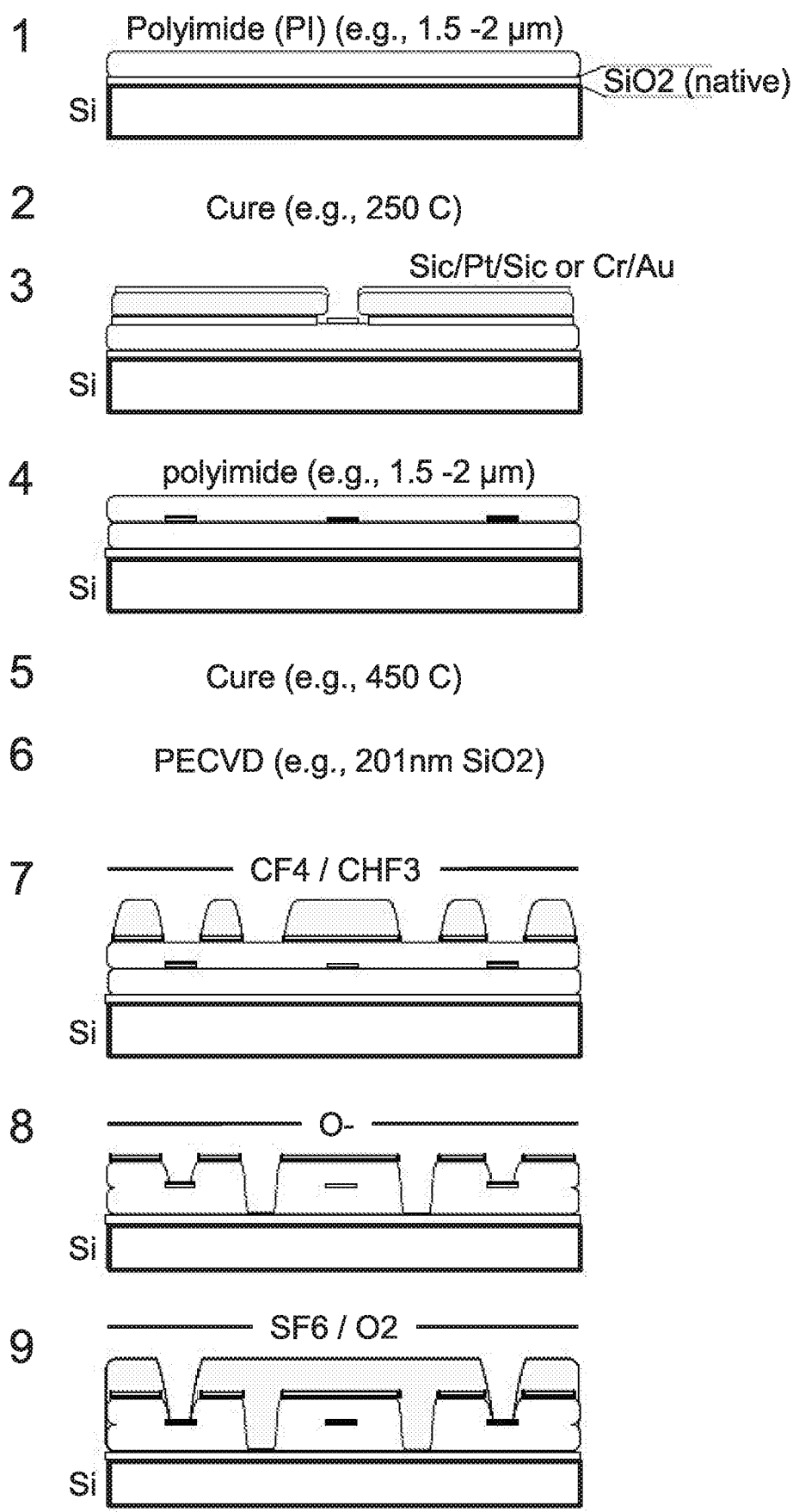
FIG. 8A-8C depict illustrative examples of methods to fabricate a subject implantable device.
Figure 8B:
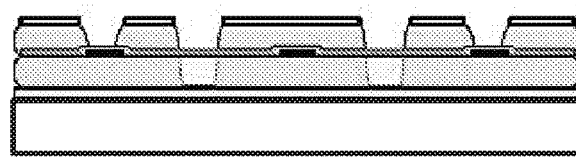
Figure 8B:
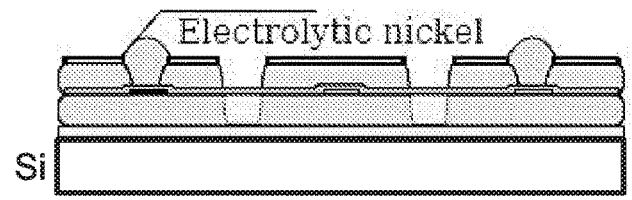
Figure 8B:
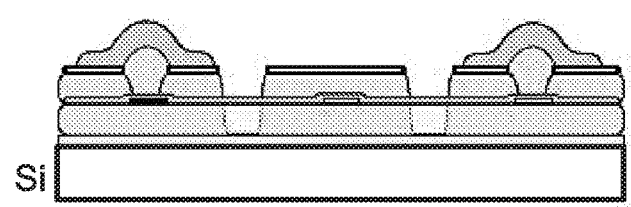
Figure 8B:
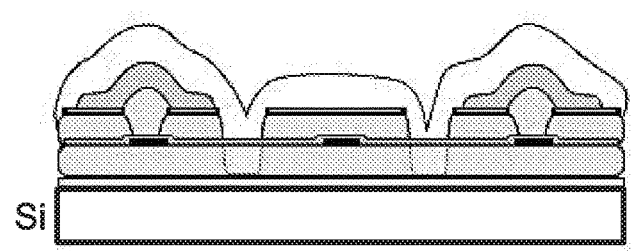
Figure 8B:
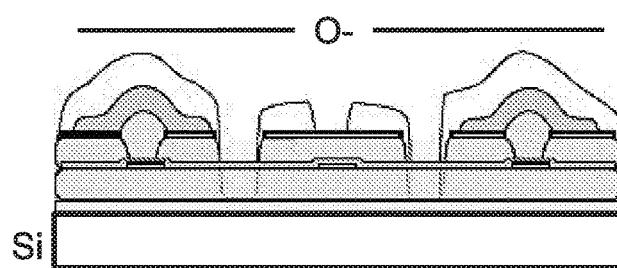
Figure 8B:
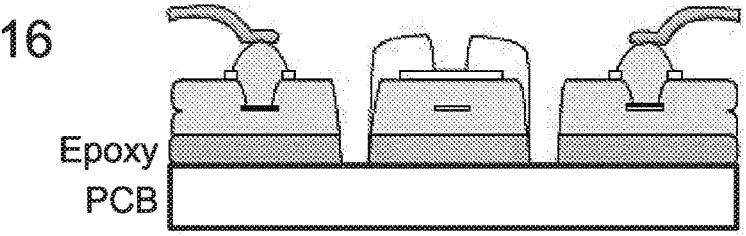
Figure 8C:
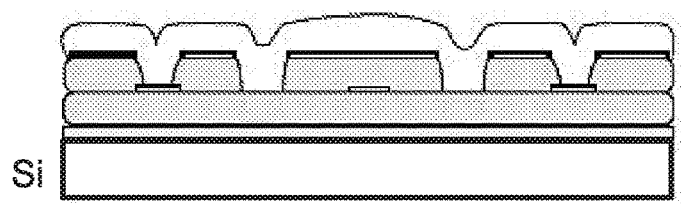
Figure 8C:
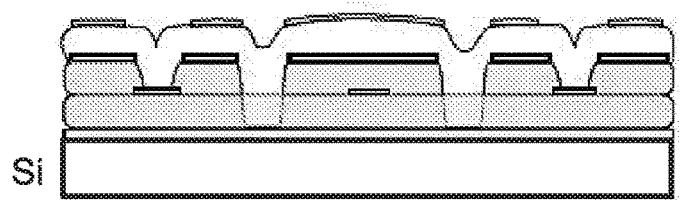
Figure 8C:
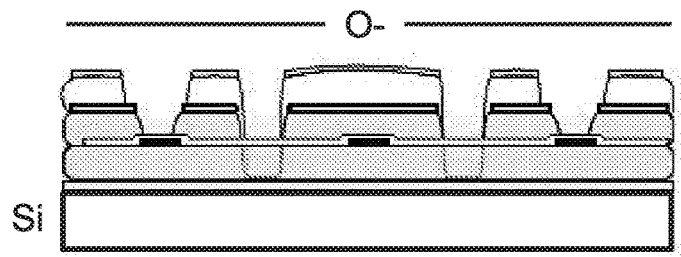
Figure 8C:
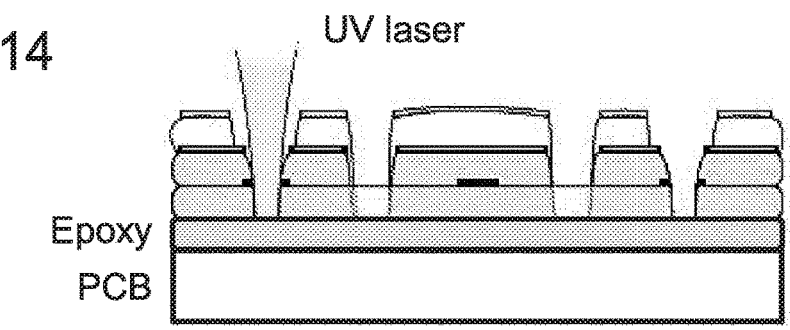
Figure 8C:
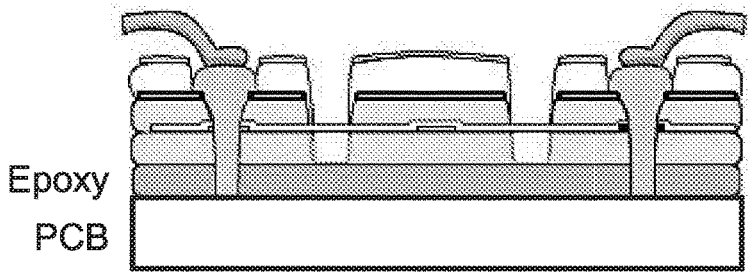

FIG. 8A-8C depict illustrative examples of methods used to fabricate a subject implantable device (i.e., implantable device fabrication), in this case a plurality of implantable devices are fabricated as a cartridge that includes a flexible backing sheet comprising parylene. FIG. 8A depicts the first nine steps that were used to generate the implantable devices (as depicted in FIG. 8B-8C). For example, two different illustrative example methods are presented, the first nine steps for both example methods are presented in FIG. 8A, and the remaining steps (steps ten to sixteen) of example method 1 are presented in FIG. 8B, while the remaining steps (steps ten to fifteen) of example method 2 are presented in FIG. 8C. For both presented example methods, the implantable devices were produced via etching (e.g., dry and/or wet etching). See Example 2 in the Experimental section for a description of an example protocol that was used.

Insertion Needle

A subject insertion needle includes an engagement feature that corresponds to an engagement feature of a subject implantable device. An engagement feature of a subject insertion needle can reversibly engage the corresponding engagement feature of the implantable device. In some cases, the engagement feature of the insertion needle (e.g., a flange) penetrates through the engagement feature (e.g., a loop) of the implantable device. In some cases, the distal end of the insertion needle penetrates through the engagement feature (e.g., a loop) of the implantable device. In some cases, the engagement feature of the insertion needle (e.g., a flange) and the distal end of the insertion needle both penetrate through the engagement feature (e.g., a loop) of the implantable device.

In some embodiments, the engagement feature of an insertion needle is a flange (e.g., a protrusion). A flange can be formed in a variety of ways and any convenient flange can suffice. Suitable illustrative examples of a flange include, but are by no means limited to the following. In some cases, a flange is a notch (e.g., carved into the body of the insertion needle) (e.g., see FIG. 3A-3E for an example). In some cases, the flange is a ledge (e.g., which in some cases can be formed from a step in the diameter of the insertion needle (e.g., see to FIG. 4A-4B). In some cases, the engagement feature (a flange) of the insertion needle is formed when the insertion needle comprises two wires connected to one another and one of the two wires is shorter than the other such that the distal end of the shorter wire forms the flange. In some such cases, the two wires are straight and in some such cases the wires are twisted (e.g., twisted together forming a helix, or one is straight and the other is twisted about the straight wire).

As noted above, in some cases, the insertion needle comprises two wires connected to one another. In some cases, the wires are straight. In some cases, the wires are twisted. The term "twisted" encompasses situations in which (i) one of the two wires is straight while the other wire is twisted about the straight wire, and (ii) both wires are twisted about one another (neither is straight) forming a helix. Thus, the phrases "twisted together forming a helix" and "twisted about one another forming a helix" are used interchangeably to describe situation (ii) above. In some cases, the engagement feature (a flange) of the insertion is formed when the insertion needle comprises two wires connected to one another, one of the two wires is shorter than the other such that the distal end of the shorter wire forms the flange, and the two wires are twisted together forming a helix (e.g., see FIG. 5A-5D).

In some cases, an insertion needle includes three wires. In some such cases, the third wire is shorter than the other two and does not enter the biological tissue upon insertion of the insertion needle (e.g., upon insertion of a device-loaded insertion needle). For example, a third wire can be used to provide support to the insertion needle, e.g., to prevent buckling during insertion and/or retraction of the insertion needle (e.g., during ballistic retraction).

In some case, while the insertion needle and implantable device are engaged, the flange penetrates through the engagement feature of the implantable device while the distal end of the insertion needle does not (e.g., refer to FIG. 3A-3E). Although such an embodiment is depicted in FIG. 3A-3E, but is not depicted in FIG. 4A-4B or FIG. 5A-5D, such an embodiment is possible with any desired insertion needle geometry (e.g., for any convenient insertion needle geometry, the flange can be designed such that, while engaged, the flange penetrates through the engagement feature of the implantable device while the distal end of the insertion needle does not).

In some case, while the insertion needle and implantable device are engaged, the distal end of the insertion needle penetrates through the engagement feature of the implantable device (e.g., refer to FIGS. 4A-4B and FIGS. 5A-5D). Although such an embodiment is depicted in FIGS. 4A-4B and FIGS. 5A-5D, but is not depicted in FIGS. 3A-3E, such an embodiment is possible with any desired insertion needle geometry (e.g., for any convenient insertion needle geometry, the insertion needle can be designed such that, while engaged, the distal end of the insertion needle penetrates through the engagement feature of the implantable device).

In some embodiments, the engagement feature of an insertion needle is simply the geometry of the insertion needle (e.g., without any need for a flange/protrusion). For example, if the engagement feature of the implantable device is a loop, an insertion needle that is tapered from a point at the distal end to a region more proximal where the diameter becomes equal to or greater than the diameter of the engagement feature of the implantable device, the insertion needle can engage implantable device with no need for flange, the diameter of the needle itself serves as an engagement feature that can reversibly engage the implantable device (e.g., when moving in one direction such as the direction of insertion, the insertion needle and implantable device would remain engaged but when moving in the opposite direction during retraction, the insertion needle and implantable device would be allowed to disengage.

In some embodiments, the engagement feature of the insertion needle is positioned in a distal region of the insertion needle. As used herein the "distal region" is the distal-most 25% of the insertion needle (relative to the entire length of the insertion needle). To be clear the distal end of the insertion need is the tip of the needle that penetrated into the target tissue (e.g., the biological tissue).

In some cases, the engagement feature of the insertion needle is positioned in the distal region of the insertion needle, but not at the distal end (meaning, the engagement feature is set back from the distal tip, i.e., the engagement feature is set back from the distal end). For example, in some cases, the engagement feature of the insertion needle is positioned in the distal region of the insertion needle, but is not present in the distal most 10% of the distal region. In some cases, the engagement feature of the insertion needle is positioned in the distal region of the insertion needle, but is not present in the distal most 5% of the distal region. In some cases, the engagement feature of the insertion needle is positioned in the distal region of the insertion needle, but is not present in the distal most 3% of the distal region. In some cases, the engagement feature of the insertion needle is positioned in the distal region of the insertion needle, but is not present in the distal most 2% of the distal region. In some cases, the engagement feature of the insertion needle is positioned in the distal region of the insertion needle, but is not present in the distal most 1% of the distal region. In some cases, the engagement feature of the insertion needle is positioned in the distal region of the insertion needle, but is not present in the distal most 0.5% of the distal region.

In some cases, the engagement feature of the insertion needle is positioned at least at least 5 μm away from the distal end of the insertion needle (e.g., at least 10 μm, at least 15 μm, at least 20 μm, at least 25 μm, at least 30 μm, at least 35 μm, at least 40 μm, at least 45 μm, or at least 50 μm away from the distal end). In some cases, the engagement feature of the insertion needle is positioned at least at least 10 μm away from the distal end of the insertion needle (e.g., at least 15 μm, at least 20 μm, at least 25 μm, at least 30 μm, at least 35 μm, at least 40 μm, at least 45 μm, or at least 50 μm away from the distal end). In some cases, the engagement feature of the insertion needle is positioned at least at least 20 μm away from the distal end of the insertion needle (e.g., at least 25 μm, at least 30 μm, at least 35 μm, at least μm, at least 45 μm, or at least 50 μm away from the distal end).

In some cases, the engagement feature of the insertion needle is positioned in the distal region of the insertion needle, but is positioned at least 5 μm away from the distal end (e.g., at least 10 μm, at least 15 μm, at least 20 μm, at least 25 μm, at least 30 μm, at least 35 μm, at least 40 μm, at least 45 μm, or at least 50 μm away from the distal end). In some cases, the engagement feature of the insertion needle is positioned in the distal region of the insertion needle, but is positioned at least 10 μm away from the distal end (e.g., at least 15 μm, at least μm, at least 25 μm, at least 30 μm, at least 35 μm, at least 40 μm, at least 45 μm, or at least 50 μm away from the distal end). In some cases, the engagement feature of the insertion needle is positioned in the distal region of the insertion needle, but is positioned at least 20 μm away from the distal end (e.g., at least 15 μm, at least 20 μm, at least 25 μm, at least 30 μm, at least 35 μm, at least 40 μm, at least 45 μm, or at least 50 μm away from the distal end).

In some cases, the engagement feature of the insertion needle is positioned within 100 μm of the distal end of the insertion needle (e.g., within 90 μm, 80 μm, 70 μm, 60 μm, 50 μm, 40 μm, 30 μm, 20 μm, or 10 μm, of the distal end of the insertion needle). In some cases, the engagement feature of the insertion needle is positioned within 100 μm of the distal end of the insertion needle (e.g., within 90 μm, 80 μm, 70 μm, 60 μm, 50 μm, 40 μm, 30 μm, 20 μm, or 10 μm, of the distal end of the insertion needle), but is not positioned at the distal end of the insertion needle. For example in some cases, the engagement feature of the insertion needle is positioned within 100 μm of the distal end of the insertion needle (e.g., within 90 μm, 80 μm, 70 μm, 60 μm, 50 μm, 40 μm, 30 μm, 20 μm, or 10 μm, of the distal end of the insertion needle), and is positioned at least 5 μm away from the distal end (e.g., at least 10 μm, at least 15 μm, at least 20 μm, at least 25 μm, at least 30 μm, at least 35 μm, at least 40 μm, at least 45 μm, or at least 50 μm away from the distal end). In some cases, the engagement feature of the insertion needle is positioned within 100 μm of the distal end of the insertion needle (e.g., within 90 μm, 80 μm, 70 μm, 60 μm, 50 μm, 40 μm, 30 μm, 20 μm, or 10 μm, of the distal end of the insertion needle), and is positioned at least 10 μm from the distal end of the insertion needle. In some cases, the engagement feature of the insertion needle is positioned within 100 μm of the distal end of the insertion needle (e.g., within 90 μm, 80 μm, 70 μm, 60 μm, 50 μm, 40 μm, 30 μm, 20 μm, or 10 μm, of the distal end of the insertion needle), and is positioned at least 20 μm from the distal end of the insertion needle. In some cases, the engagement feature of the insertion needle is positioned within 80 μm of the distal end of the insertion needle (e.g., within 70 μm, 60 μm, 50 μm, 40 μm, 30 μm, 20 μm, or 10 μm, of the distal end of the insertion needle), and is positioned at least 10 μm from the distal end of the insertion needle. In some cases, the engagement feature of the insertion needle is positioned within 80 μm of the distal end of the insertion needle (e.g., within 70 μm, 60 μm, 50 μm, 40 μm, 30 μm, 20 μm, or 10 μm, of the distal end of the insertion needle), and is positioned at least 20 μm from the distal end of the insertion needle.

In some embodiments, as described below, the insertion needle is rotated about its longitudinal axis during insertion and/or retraction. In some cases, an insertion needle having a helical geometry (e.g., in a case where the insertion needle comprises two wires twisted around one another forming a helix) can facilitate such rotation. Thus, in some cases, a subject insertion needle has a helical geometry. In some cases, a subject insertion needle includes two wires twisted around one another forming a helix.

In some embodiments, the insertion needle is made of a rigid material (e.g., tungsten) and therefore the insertion needle is rigid (stiff). Thus, in some cases, the insertion needle comprises a rigid material (e.g., tungsten). Any convenient stiff, strong material (e.g., having a relatively high Young's modulus) can be used for fabricating the needle (i.e., the insertion needle can comprise any convenient stiff, strong material). Suitable materials include, but are not limited to: tungsten, tungsten carbide, iridium, carbon nanotube, boron, boride (e.g., BN), ceramic oxides and nitrides, and composite materials.

Dimensions

A subject insertion needle can have a larger variety of dimensions and geometries. Any convenient dimensions and/or geometries can be used. As used below, the term "maximum diameter" is used in the following context to mean the diameter of the insertion needle at the point along its length (of the portion of the insertion needle that is inserted or is to be inserted in a biological tissue) at which it is its widest. For example, in some cases, the insertion needle has one diameter at the point of contact with the biological tissue, but another length farther up the insertion needle (e.g., due to a change in geometry of the insertion needle), and the 'maximum diameter' describes the diameter when the insertion needle is its widest (along the portion of the needle that is inserted or is to be inserted). Likewise, the term "maximum cross sectional area" is used to mean the cross sectional area of the insertion needle at the point along its length (of the portion of the insertion needle that is inserted or is to be inserted in a biological tissue) at which it is its biggest (i.e., the 'maximum cross sectional area' describes the cross-sectional area when the insertion needle is its widest, along the portion of the needle that is inserted or is to be inserted).

In some cases, the insertion needle has a maximum diameter (e.g., along the length of insertion) of 80 μm or less (e.g., 70 μm or less, 65 μm or less, 60 μm or less, 55 μm or less, 50 μm or less, 55 μm or less, 50 μm or less, 45 μm or less, 40 μm or less, 35 μm or less, 30 μm or less, or 25 μm or less). For example, in some cases, the insertion needle has a maximum diameter (e.g., along the length of insertion) of 65 μm or less. In some cases, the insertion needle has a maximum diameter (e.g., along the length of insertion) of 35 μm or less.

In some cases, the insertion needle has a maximum diameter (e.g., along the length of insertion) in a range of from 10 to 80 μm (e.g., from 10 to 70 μm, from 10 to 65 μm, from 10 to 60 μm, from 10 to 55 μm, from 10 to 50 μm, from 10 to 45 μm, from 10 to 40 μm, from 10 to 35 μm, from 15 to 80 μm from 15 to 70 μm, from 15 to 65 μm, from 15 to 60 μm, from 15 to 55 μm, from 15 to 50 μm, from 15 to 45 μm, from 15 to 40 μm, from 15 to 35 μm, from 20 to 80 μm from 20 to 70 μm, from 20 to 65 μm, from 20 to 60 μm, from 20 to 55 μm, from 20 to 50 μm, from 20 to 45 μm, from 20 to 40 μm, from 20 to 35 μm, from 25 to 80 μm from 25 to 70 μm, from 25 to 65 μm, from 25 to 60 μm, from 25 to 55 μm, from 25 to 50 μm, from 25 to 45 μm, from 25 to 40 μm, or from 25 to 35 μm). In some cases, the insertion needle has a maximum diameter (e.g., along the length of insertion) in a range of from 20 to 65 μm. In some cases, the insertion needle has a maximum diameter (e.g., along the length of insertion) in a range of from to 65 μm. In some cases, the insertion needle has a maximum diameter (e.g., along the length of insertion) in a range of from 20 to 35 μm. In some cases, the insertion needle has a maximum diameter (e.g., along the length of insertion) in a range of from 25 to 35 μm.

In some cases, the insertion needle has a maximum cross sectional area (e.g., along the length of insertion) of 5000 $\mu m^2$ or less (e.g., 4500 $\mu m^2$ or less, 4000 $\mu m^2$ or less, 3500 $\mu m^2$ or less, 3000 $\mu m^2$ or less, 2500 $\mu m^2$ or less, 2000 $\mu m^2$ or less, 1500 $\mu m^2$ or less, 1000 $\mu m^2$ or less, 800 $\mu m^2$ or less, 750 $\mu m^2$ or less, or 700 $\mu m^2$ or less). In some cases, the insertion needle has a maximum cross sectional area (e.g., along the length of insertion) of 4000 $\mu m^2$ or less (e.g., 3500 $\mu m^2$ or less, 3000 $\mu m^2$ or less, 2500 $\mu m^2$ or less, 2000 $\mu m^2$ or less, 1500 $\mu m^2$ or less, 1000 $\mu m^2$ or less, 800 $\mu m^2$ or less, 750 $\mu m^2$ or less, or 700 $\mu m^2$ or less). In some cases, the insertion needle has a maximum cross sectional area (e.g., along the length of insertion) of 3500 $\mu m^2$ or less (e.g., 3000 $\mu m^2$ or less, 2500 $\mu m^2$ or less, 2000 $\mu m^2$ or less, 1500 $\mu m^2$ or less, 1000 $\mu m^2$ or less, 800 $\mu m^2$ or less, 750 $\mu m^2$ or less, or 700 $\mu m^2$ or less). In some cases, the insertion needle has a maximum cross sectional area (e.g., along the length of insertion) of 2000 $\mu m^2$ or less (e.g., 1500 $\mu m^2$ or less, 1000 $\mu m^2$ or less, 800 $\mu m^2$ or less, 750 $\mu m^2$ or less, or 700 $\mu m^2$ or less). In some cases, the insertion needle has a maximum cross sectional area (e.g., along the length of insertion) of 1000 $\mu m^2$ or less (e.g., 800 $\mu m^2$ or less, 750 $\mu m^2$ or less, or 700 $\mu m^2$ or less).

In some cases, the insertion needle has a maximum cross sectional area (e.g., along the length of insertion) in a range of from 250 to 4000 $\mu m^2$ (e.g., from 250 to 3500 $\mu m^2$, from 250 to 3000 $\mu m^2$, from 250 to 2500 $\mu m^2$, from 250 to 3000 $\mu m^2$, from 250 to 2500 $\mu m^2$, from 250 to 2000 $\mu m^2$, from 250 to 1500 $\mu m^2$, from 250 to 1000 $\mu m^2$, from 250 to 800 $\mu m^2$, from 400 to 4000 $\mu m^2$, from 400 to 3500 $\mu m^2$, from 400 to 3000 $\mu m^2$, from 400 to 2500 $\mu m^2$, from 400 to 3000 $\mu m^2$, from 400 to 2500 $\mu m^2$, from 400 to 2000 $\mu m^2$, from 400 to 1500 $\mu m^2$, from 400 to 1000 $\mu m^2$, from 400 to 800 $\mu m^2$, from 500 to 4000 $\mu m^2$, from 500 to 3500 $\mu m^2$, from 500 to 3000 $\mu m^2$, from 500 to 2500 $\mu m^2$, from 500 to 3000 $\mu m^2$, from 500 to 2500 $\mu m^2$, from 500 to 2000 $\mu m^2$, from 500 to 1500 $\mu m^2$, from 500 to 1000 $\mu m^2$, from 500 to 800 $\mu m^2$, from 1000 to 4000 $\mu m^2$, from 1000 to 3500 $\mu m^2$, from 1000 to 3000 $\mu m^2$, from 1000 to 2500 $\mu m^2$, from 1000 to 3000 $\mu m^2$, from 1000 to 2500 $\mu m^2$, from 1000 to 2000 $\mu m^2$, from 1000 to 1500 $\mu m^2$, from 2000 to 4000 $\mu m^2$, from 2000 to 3500 $\mu m^2$, from 2000 to 3000 $\mu m^2$, from 2000 to 2500

$\mu m^2$, from 2000 to 3000 $\mu m^2$, from 2000 to 2500 $\mu m^2$, from 2500 to 4000 $\mu m^2$, from 2500 to 3500 $\mu m^2$, from 2500 to 3000 $\mu m^2$, from 2500 to 2500 $\mu m^2$, or from 2500 to 3000 $\mu m^2$).

In some cases, the insertion needle has a maximum cross sectional area (e.g., along the length of insertion) in a range of from 2000 to 4500 $\mu m^2$. In some cases, the insertion needle has a maximum cross sectional area (e.g., along the length of insertion) in a range of from 2500 to 4000 $\mu m^2$. In some cases, the insertion needle has a maximum cross sectional area (e.g., along the length of insertion) in a range of from 500 to 1000 $\mu m^2$.

As noted above in the section describing the implantable device, FIG. 2A-2C depict scale-accurate comparisons of disclosed embodiments to conventional electrodes (e.g., conventional electrodes used for deep brain stimulation). As depicted in FIG. 2A, in which four implanted subject implantable devices are shown, in some cases tissue displacement by disclosed implantable devices can be approximately 800 times less than tissue displacement by conventional electrodes. FIG. 2B-2C depicts a scale-accurate comparison of disclosed embodiments to a conventional deep brain stimulation (DBS) electrode and to a conventional "Utah Array." Depicted is a subject implantable device 1 that includes eight conduits (e.g., 8 electrodes), one embodiment of a subject insertion needle 2 that can be used to insert the implantable device 1, a subject implantable device 3 that includes one conduit (e.g., an electrode), and one embodiment of a subject insertion needle 4 that can be used to insert the implantable device 3.

See Example 3 in the Experimental section for a description of example protocols that were used to produce three different types of insertion needles, one with a flange formed from a notch carved into the body of the needle, one with a flange formed from a step in the diameter of the insertion needle, and one with a flange formed from two wires twisted together forming a helix, where one of the two wires is shorter than the other such that the distal end of the shorter wire forms the flange. Two additional example protocols are also provided: continuous-melt copper brazing, and dicing-saw notch cutting.

Methods

A subject method of implanting an implantable device into a biological tissue includes (a) reversibly engaging an engagement feature of an implantable device (e.g., as described in more detail elsewhere herein) with a corresponding engagement feature of an insertion needle (e.g., as described in more detail elsewhere herein), thereby generating a device-loaded insertion needle; (b) inserting the device-loaded insertion needle into a biological tissue to a desired depth within the tissue; and (c) retracting the insertion needle, thereby disengaging the implantable device from the insertion needle and allowing the implantable device to remain implanted in the biological tissue.

In some cases a plurality of implantable devices is implanted with the same insertion needle. Thus, the insertion needle has an engagement feature that corresponds to (can reversibly engage) the engagement feature of each of the implantable devices of the plurality of implantable devices to be implanted. In some cases, all of the implantable devices of the plurality of implantable devices will have an identical engagement feature. In some cases, all of the implantable devices of the plurality of implantable devices will have a similar engagement feature (e.g., in some cases the same type of engagement feature, in some cases the same type of engagement feature with slightly different dimensions, etc.). In some cases, two or more implantable devices of the plurality of implantable devices will have different engagement features, and this is okay as long as the engagement feature of the insertion needle can reversibly engage (and therefore corresponds to) the engagement feature of the implantable devices.

In some embodiments, when a plurality of implantable devices is implanted using the same insertion needle, an implantable device is engaged and then implanted (e.g., steps (a)-(c) above), and then the process is repeated for one or more additional implantable devices. Thus, in some cases, a plurality of implantable devices is implanted where the implantable devices are implanted one at a time.

In some cases, e.g., where the implantable device is part of a plurality of implantable devices (e.g., an implantable device cartridge, as described above), a subject method includes removing (e.g., peeling, delaminating, etc.) an implantable device from an implantable device cartridge prior to implanting the implantable device. Thus, in some cases the engaging step (step (a) above) includes removal (e.g., peeling, delaminating, breaking-away etc.) of the implantable device to be implanted from the plurality of implantable devices. In some cases where a plurality of implantable devices is implanted using the same insertion needle, and an implantable device is engaged and then implanted (e.g., steps (a)-(c) above), and then the process is repeated for one or more additional implantable devices, the engaging step (step (a) above) includes removal of the implantable device to be implanted from the plurality of implantable devices (e.g., peeling, delaminating, breaking-away, etc. an implantable device from an implantable device cartridge).

As one of the advantages of the provided methods is to reduce the level of invasiveness relative to other methods, in some embodiments, the total tissue displacement resulting from a subject implanting method is less than 2% (e.g., less than 1.8%, less than 1.6%, less than 1.4%, less than 1.2%, less than 1, less than 0.8%, less than 0.6%, or less than 0.4%). In some embodiments, the total tissue displacement resulting from a subject implanting method is in a range of from 0.2% to 2% (e.g., 0.2% to 1.8%, 0.2% to 1.6%, 0.2% to 1.4%, 0.2% to 1.2%, 0.2% to 1%, 0.2% to 0.8%, 0.2% to 0.6%, 0.2% to 0.4%, 0.4% to 2%, 0.4% to 1.8%, 0.4% to 1.6%, 0.4% to 1.4%, 0.4% to 1.2%, 0.4% to 1%, 0.4% to 0.8%, 0.4% to 0.6%, 0.6% to 2%, 0.6% to 1.8%, 0.6% to 1.6%, 0.6% to 1.4%, 0.6% to 1.2%, 0.6% to 1%, or 0.6% to 0.8%). The percentages above refer to the fraction of tissue displaced relative to the total volume and/or cross-section of tissue covered by implanted implantable devices. As an illustrative example, one might implant a plurality of implantable devices across 3 $cm^2$ of brain tissue (e.g., 3 $cm^2$ of cortex) while displacing only 0.8% of the tissue in that same region.

Biological Tissue

An implantable device can be implanted into any convenient biological tissue using the methods provided herein, and the implantable devices can be implanted at any desired depth. Examples of suitable target biological tissues (into which implantable device can be implanted using the subject methods, components, and systems) include but are not limited to: Brain, muscle, liver, pancreas, spleen, kidney, bladder, intestine, heart, stomach, skin, and colon. In some cases, the targeted biological tissue is a brain. The biological tissue can be from any multicellular organism including but not limited to invertebrates, vertebrates, fish, birds, mammals, rodents (e.g., mice, rats), ungulates, cows, sheep, pigs, horses, non-human primates, and humans. In some cases, the biological tissue is ex vivo (e.g., a tissue explant). In some cases, the biological tissue is in vivo (e.g., the method is a surgical procedure performed on a patient).

Rotation

In some embodiments, as described below, the insertion needle is rotated about its longitudinal axis during insertion and/or retraction. In some cases, an insertion needle having a helical geometry (e.g., in a case where the insertion needle comprises two wires twisted around one another forming a helix) can facilitate such rotation. Thus, in some cases, a subject insertion needle has a helical geometry. In some cases, a subject insertion needle includes two wires twisted around one another forming a helix.

Speed of Insertion

In some cases, the insertion speed (the speed at which the insertion needle penetrates into the biological tissue to reach the desired tissue depth) is controlled (e.g., in some cases controlled by a processor, in some cases controlled by a human operator, etc.).

In some cases, the insertion speed is less than 1000 μm per second (e.g., less than 900 μm per second, 800 μm per second, 600 μm per second, or 500 μm per second).

In some cases, the insertion speed is at least 200 μm per second (e.g., at least 300 μm per second, 400 μm per second, 500 μm per second, 600 μm per second, or 700 μm per second).

In some cases, the insertion speed is in a range of from 200 to 1000 μm per second (e.g., in a range of from 200 to 900 μm per second, 200 to 800 μm per second, 200 to 700 μm per second, 200 to 600 μm per second, 300 to 1000 μm per second, 300 to 900 μm per second, 300 to 800 μm per second, 300 to 700 μm per second, 300 to 600 μm per second, 400 to 1000 μm per second, 400 to 900 μm per second, 400 to 800 μm per second, 400 to 700 μm per second, 400 to 600 μm per second, 500 to 1000 μm per second, 500 to 900 μm per second, 500 to 800 μm per second, 500 to 700 μm per second, 500 to 600 μm per second, 600 to 1000 μm per second, 600 to 900 μm per second, 600 to 800 μm per second, 700 to 1000 μm per second, 700 to 900 μm per second, or 700 to 800 μm per second).

Speed/Acceleration of Retraction

In some cases, the retraction speed (the speed at which the insertion needle retracts from, i.e., is removed from, the biological tissue) is controlled (e.g., in some cases controlled by a processor, in some cases controlled by a human operator, etc.). For example, in some cases, adhesive and/or cohesive forces exist between the insertion needle and the implantable device of a device-loaded insertion needle, and the implantable device can in some cases tend to remain engaged with the insertion needle upon retraction (e.g., upon the initiation of retraction). In some cases, it will be desirable to control the speed of retraction such that the initiation of retraction is fast enough to disengage the implantable device from the insertion needle. For example, in some cases, the retraction can be "ballistic." For example, in some cases, a rapid retraction speed (e.g., a jerk, a rapid speed of initiation of retraction, e.g., high acceleration) is desirable. Any convenient methodology can be used to achieve such an end (e.g., a spring-loaded mechanism can be utilized to achieve rapid initiation of retraction, e.g., achieve a high acceleration). For example, in some cases, the insertion needle rides in a cartridge attached to a shuttle driven by a spring-loaded concentric slug with slow depth actuation.

In some cases, retraction is performed with an acceleration of the insertion needle of at least 50,000 meters per second squared (m/s$^2$) (e.g., at least 50,000 m/s$^2$, at least 60,000 m/s$^2$, at least 70,000 m/s$^2$, at least 80,000 m/s$^2$, at least 85,000 m/s$^2$, at least 90,000 m/s$^2$, at least 95,000 m/s$^2$, or at least 100,000 m/s$^2$). In some cases, retraction is performed with an acceleration of the insertion needle in a range of from 50,000 to 200,000 m/s$^2$ (e.g., from 50,000 to 150,000 m/s$^2$, from 50,000 to 125,000 m/s$^2$ from 50,000 to 115,000 m/s$^2$, from 50,000 to 100,000 m/s$^2$, from 60,000 to 200,000 m/s$^2$ from 60,000 to 150,000 m/s$^2$, from 60,000 to 125,000 m/s$^2$, from 60,000 to 115,000 m/s$^2$ from 60,000 to 100,000 m/s$^2$, from 70,000 to 200,000 m/s$^2$, from 70,000 to 150,000 m/s$^2$ from 70,000 to 125,000 m/s$^2$, from 70,000 to 115,000 m/s$^2$, from 70,000 to 100,000 m/s$^2$ from 80,000 to 200,000 m/s$^2$, from 80,000 to 150,000 m/s$^2$, from 80,000 to 125,000 m/s$^2$ from 80,000 to 115,000 m/s$^2$, from 80,000 to 100,000 m/s$^2$, from 90,000 to 200,000 m/s$^2$ from 90,000 to 150,000 m/s$^2$, from 90,000 to 125,000 m/s$^2$, from 90,000 to 115,000 m/s$^2$ or from 90,000 to 100,000 m/s$^2$).

In some cases, the retraction speed (the speed at which the insertion needle is retracted) reaches at least 0.4 meters per second (m/s) (e.g., at least 0.5 m/s, at least 0.6 m/s, at least 0.7 m/s, at least 0.8 m/s, at least 0.9 m/s, at least 1 m/s, at least 1.5 m/s, at least 2 m/s, or at least 2.5 m/s). In some cases, the retraction speed (the speed at which the insertion needle is retracted) is in a range of from 0.4 to 3 m/s (e.g., from 0.4 to 2.5 m/s, from 0.4 to 2 m/s, from 0.4 to 1.5 m/s, from 0.4 to 1 m/s, from 0.5 to 3 m/s, from 0.5 to 2.5 m/s, from 0.5 to 2 m/s, from 0.5 to 1.5 m/s, from 0.5 to 1 m/s, from 0.6 to 3 m/s, from 0.6 to 2.5 m/s, from 0.6 to 2 m/s, from 0.6 to 1.5 m/s, from 0.6 to 1 m/s, from 0.7 to 3 m/s, from 0.7 to 2.5 m/s, from 0.7 to 2 m/s, from 0.7 to 1.5 m/s, from 0.7 to 1 m/s, from 0.8 to 3 m/s, from 0.8 to 2.5 m/s, from 0.8 to 2 m/s, from 0.8 to 1.5 m/s, from 0.8 to 1 m/s, from 0.9 to 3 m/s, from 0.9 to 2.5 m/s, from 0.9 to 2 m/s, from 0.9 to 1.5 m/s, from 0.9 to 1 m/s, from 1 to 3 m/s, from 1 to 2.5 m/s, from 1 to 2 m/s, or from 1 to 1.5 m/s).

In some cases, the retraction speed is greater than the insertion speed. For example in some cases, the ratio of retraction speed to insertion speed is 1.05 or greater (e.g., 1.1 or greater, 1.2 or greater, 1.3 or greater, 1.5 or greater, 1.8 or greater, 2 or greater, 2.5 or greater, 3 or greater, 5 or greater, 10 or greater, 20 or greater, 30 or greater, 50 or greater, 100 or greater, etc.). In some cases, the ratio of retraction speed to insertion speed is in a range of from 1.05 to 100 (e.g., 2 to 100, 5 to 100, 20 to 100, 50 to 100, 2 to 50, 5 to 50, 10 to 50, 20 to 50, 2 to 30, 5 to 30, or 10 to 30).

Figure 9A:
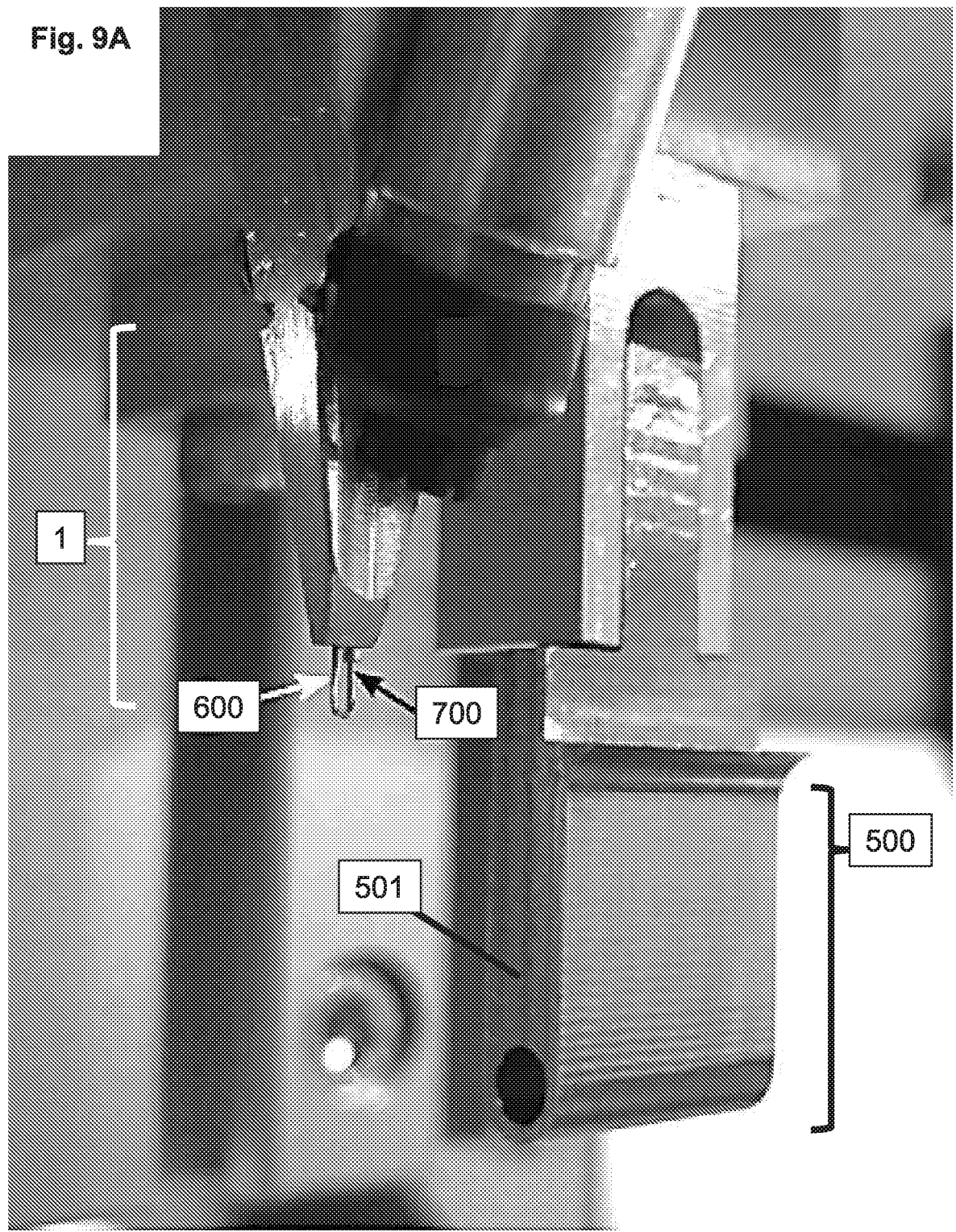

FIG. 9A-9F show photographs (successful working examples) of a subject system performing a subject method (e.g., in this case inserting a plurality of implantable devices into agar as a substitute for a biological tissue). The shown system includes an insertion device 1 that includes a brake 600 and a cannula 700 (through which an insertion needle is extended), as well as an implantable device cartridge 500. The shown cartridge 500 includes: (i) a flexible backing sheet (made of parylene) to which a plurality of implantable devices is adhered, and (ii) a solid support 501 for the flexible backing sheet. Shown in FIG. 9E is a device-loaded insertion needle 300 extending through the cannula 700 out from the insertion device 1 to implant an implantable device (in this case the implantable device includes an electrode connected to a wire 240). The brake 600 in FIG. 9A-9F can be used to prevent the wire 240 from laterally slicing into the target tissue (agar in this case). FIG. 9F shows the brake 600 swinging out of the way once the implantable device has been implanted.

Figure 10A:
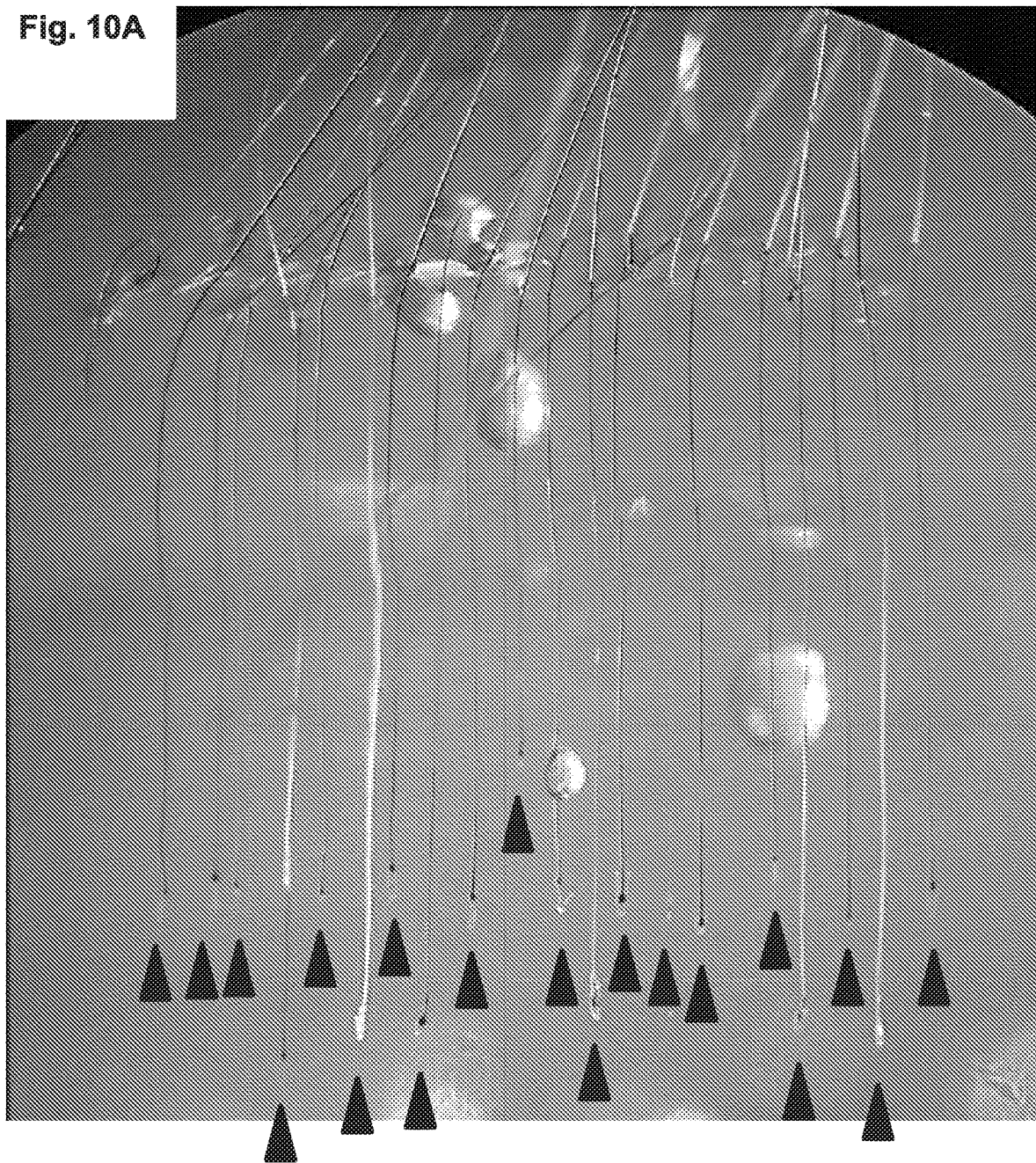
FIG. 10A-10E are pictures of implantable devices, each of which include a wire in this case, successfully implanted into agar (as a substitute for biological tissue) and into brain tissue using the systems and methods disclosed herein.
Figure 10B:
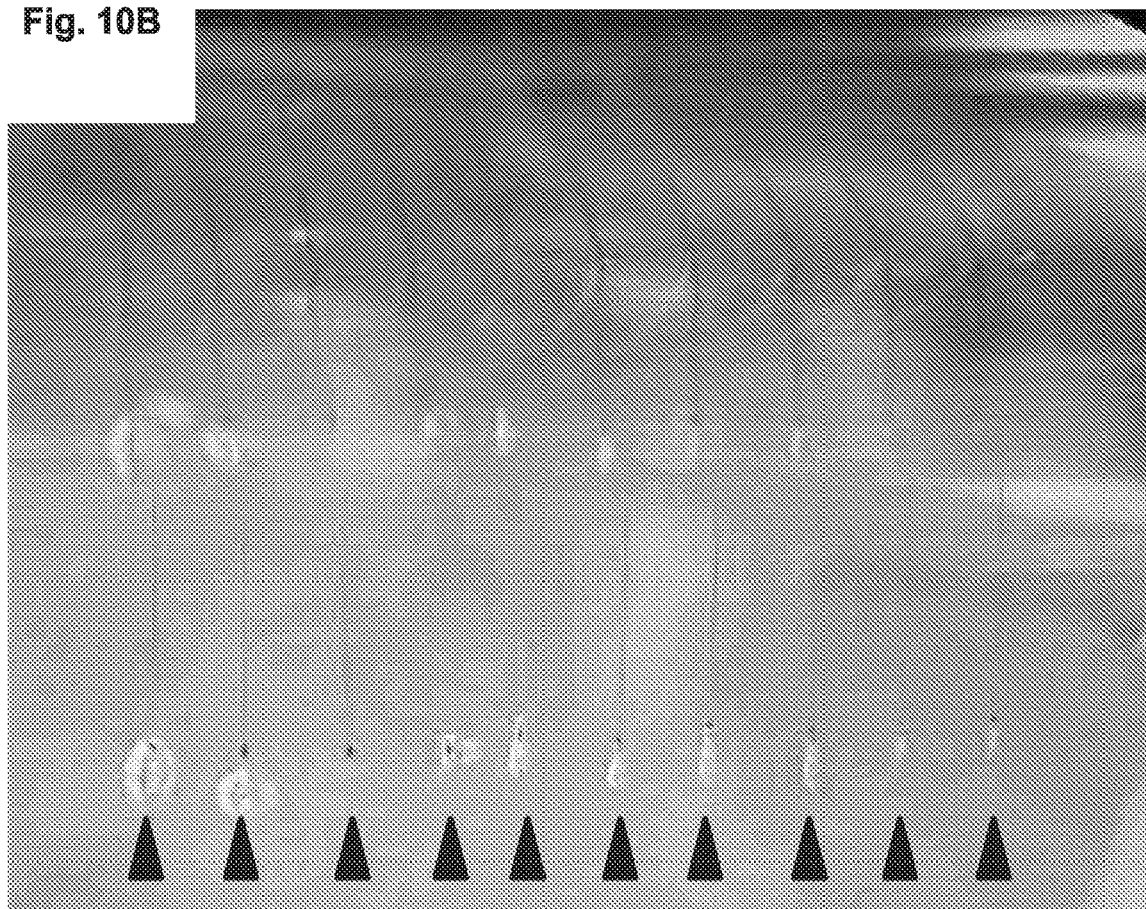
Figure 10B:
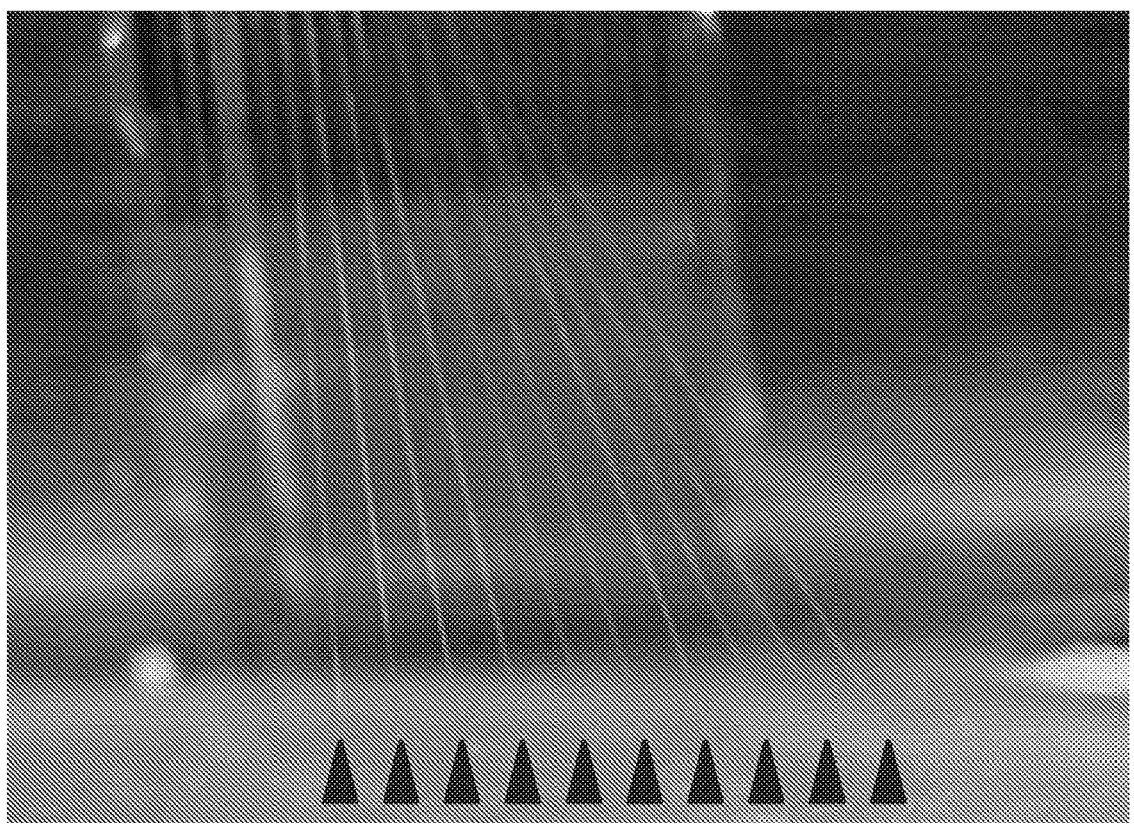
Figure 10C:
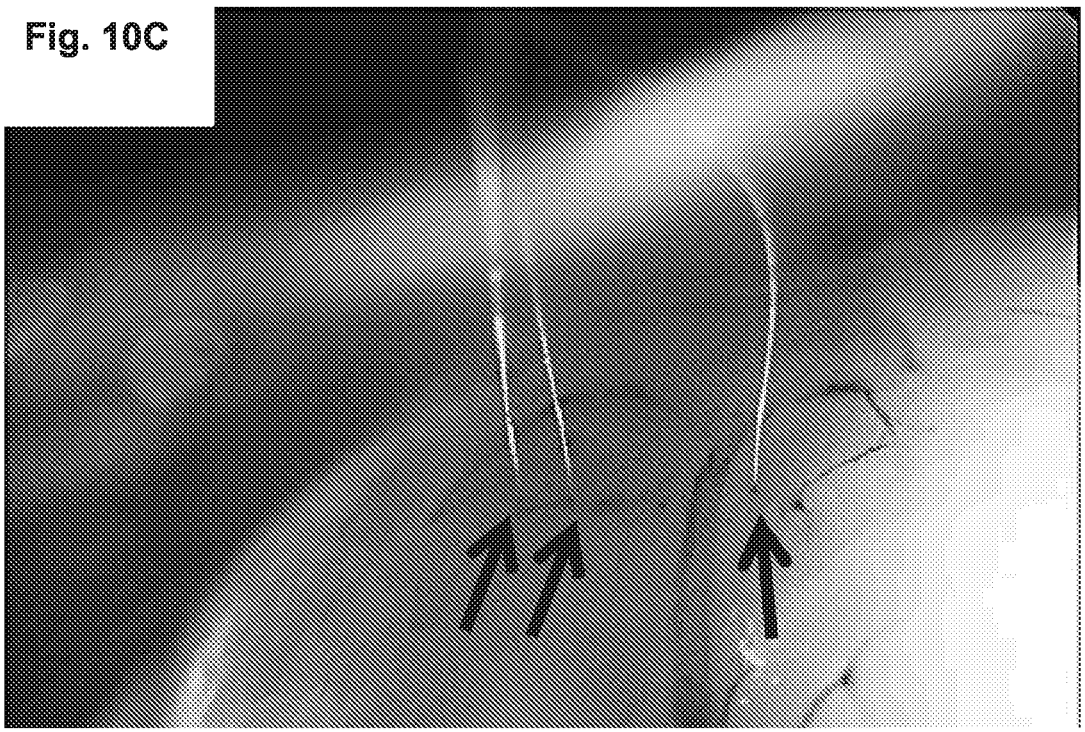
Figure 10D:
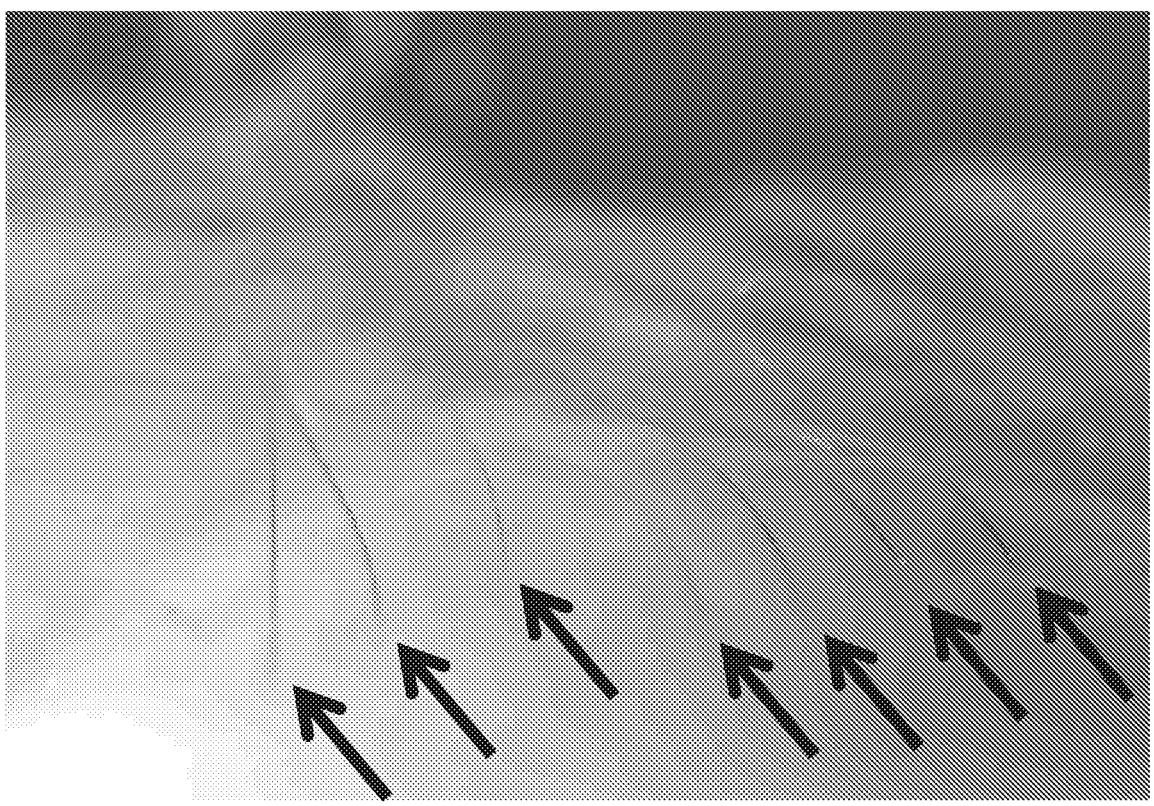
Figure 10E:

FIG. 10A-10E show photographs (successful working examples) of implantable devices (having electrodes, each connected to a respective wire) that were successfully implanted using a subject system. FIG. 10A-10B demonstrate successful implantation of a plurality of implantable devices into agar (as a substitute for a biological tissue). FIG. 10A is a picture demonstrating successful implantation of twenty implantable devices (each of which includes an electrode and a connected wire) at 500 µm spacing in two rows into 0.6% w/v agar (as an illustrative substitute for a biological tissue). FIG. 10B is a picture demonstrating successful implantation of ten implantable devices (each of which includes an electrode and a connected wire) 200 µm spacing into agar (as an illustrative substitute for a biological tissue). Top: view of implanted implantable devices in agar. Bottom: view of wires outside of the agar that connect to the implanted implantable devices. FIG. 10C is a picture of three implantable devices (each of which includes an electrode and a connected wire) successfully implanted into a zebra finch brain (ex vivo). FIG. 10D is a picture of seven implantable devices (each of which includes an electrode and a connected wire) successfully implanted into the opposite hemisphere of the brain shown in FIG. 100. FIG. 10F is a picture of four implantable devices (each of which includes an electrode and a connected wire) successfully implanted into a rat brain.

Systems

Also provided are systems for performing the methods above. A subject system can include any combination of the components described above. For example, in some embodiments, a subject system (e.g., a system for implanting an implantable device) includes a subject implantable device (e.g., as described above) and a subject insertion needle (e.g., as described above). In some cases the system includes a device-loaded insertion needle (i.e., an insertion needled engaged with an implantable device via the corresponding engagement features, described above).

In some cases, a subject system includes an insertion device, which can be any convenient device used to support the system (e.g., see FIG. 1 and FIG. 9A-9F). For example, an insertion device can be a solid support onto which the insertion needle is mounted (e.g., the insertion needled can be mounted into a cannula of the insertion device), and in some cases the insertion needle can be manipulated (e.g., extended and retracted, moved into position) using the insertion device and/or can be manipulated by moving the insertion device. In some cases, a system includes a brake, which can be used (i) to prevent a wire (e.g, a wire that is connected to a subject implantable device) from laterally slicing into the target tissue (the tissue into which the implantable device(s) are to be implanted) and/or (ii) to help maintain engagement between the insertion needle and the implantable device (i.e., to keep an engaged implantable device from falling off the insertion needle prior insertion) (e.g., via a pinch-grip between the brake and insertion needle cannula). For an example, see Example 1 below as well as FIG. 9A-9F. In some cases, the insertion device includes the brake.

In some cases, the insertion device includes a cannula through which an insertion needle is extended into the biological tissue. In some cases the cannula is used to pierce and penetrate into the biological tissue (e.g., the cannula can be sharp and therefore configured to pierce target tissue), and the insertion needle then extends from the cannula into the biological tissue. In some cases, the cannula does not pierce the target tissue. In some cases, the cannula comes into contact with a target tissue but does not penetrate into the tissue (i.e., does not pierce the tissue) (e.g., does not have a sharp edge, e.g., is blunt). In some cases, the cannula does not come into contact with a target tissue.

In some cases, the insertion needle can be manipulated by one or more micromanipulators. As such, in some cases, a subject system includes one or more micromanipulators configured to manipulate a subject insertion needle. In some cases when a system in includes an insertion device, the system also includes one or more micromanipulators for maneuvering the insertion device. In some cases, one or more micromanipulators are controlled by a processor (e.g., are under automated control, e.g., are operably connected to a processor).

As noted above, FIG. 9A-9F show photographs (successful working examples) of a subject system performing a subject method (e.g., in this case inserting a plurality of implantable devices into agar as a substitute for a biological tissue). The shown system includes an insertion device 1 that includes a brake 600 and a cannula 700 (through which an insertion needle is extended), as well as an implantable device cartridge 500. The shown cartridge 500 includes: (i) a flexible backing sheet (made of parylene) to which a plurality of implantable devices is adhered, and (ii) a solid support 501 for the flexible backing sheet. Shown in FIG. 9E is a device-loaded insertion needle 300 extending through the cannula 700 out from the insertion device 1 to implant an implantable device (in this case the implantable device includes an electrode connected to a wire 240). The brake 600 in FIG. 9A-9F can be used to prevent the wire 240 from laterally slicing into the target tissue (agar in this case). FIG. 9F shows the brake 600 swinging out of the way once the implantable device has been implanted.

As noted above, FIG. 10A-10E show photographs (successful working examples) of implantable devices (having electrodes, each connected to a respective wire) that were successfully implanted using a subject system. FIG. 10A-10B demonstrate successful implantation of a plurality of implantable devices into agar (as a substitute for a biological tissue). FIG. 10A is a picture demonstrating successful implantation of twenty implantable devices (each of which includes an electrode and a connected wire) at 500 µm spacing in two rows into 0.6% w/v agar (as an illustrative substitute for a biological tissue). FIG. 10B is a picture demonstrating successful implantation of ten implantable devices (each of which includes an electrode and a connected wire) 200 µm spacing into agar (as an illustrative substitute for a biological tissue). Top: view of implanted implantable devices in agar. Bottom: view of wires outside of the agar that connect to the implanted implantable devices. FIG. 10C is a picture of three implantable devices (each of which includes an electrode and a connected wire) successfully implanted into a zebra finch brain (ex vivo). FIG. 10D is a picture of seven implantable devices (each of which includes an electrode and a connected wire) successfully implanted into the opposite hemisphere of the brain shown in FIG. 100. FIG. 10F is a picture of four implantable devices (each of which includes an electrode and a connected wire) successfully implanted into a rat brain.

In some embodiments, a subject system is configured for retracting the insertion needle at a high speed. For example, in some cases, a rapid retraction speed (e.g., a rapid speed of initiation of retraction) is desirable. In some cases, the system is configured for ballistic retraction of an insertion needle (e.g., as discuss elsewhere herein). Any convenient methodology/configuration can be used to achieve such an end (e.g., a spring-loaded mechanism can be utilized to achieve rapid initiation of retraction). For example, in some cases, the insertion needle rides in a shuttle driven by a spring-loaded concentric slug with slow depth actuation.

Computers

In some cases, manipulation of a subject insertion needle (and/or a subject insertion device) is controlled by a processor (e.g., in some cases can be automated). In some cases, manipulation of a subject insertion needle (and/or a subject insertion device) is controlled by a plurality of processors (e.g., two or more, three or more, four or more, 2, 3, 4, 5, etc.) (e.g., in some cases the processors can be automated). Thus, in some cases, a subject system includes a processor (e.g., housed in a computer, as part of a computer system, etc.) configured to manipulate the motion of an insertion device and/or an insertion needle. In some cases, a processor can be configured to control the speed of insertion and/or the speed of retraction of the insertion needle as describe elsewhere herein. For example, in some cases, a processor is configured to retract the insertion needle at a greater speed than the speed at which the insertion needle is inserted. In some cases, manipulation of a subject insertion needle (and/or a subject insertion device) is controlled by more than one processor (e.g., three processors: one dedicated to retraction of the insertion needle, one dedicated to servo/stepper axes, and one dedicated to CV for targeting the needle).

In some cases, a processor is configured to retract the insertion needle with an acceleration of at least 50,000 meters per second squared ($m/s^2$) (e.g., at least 50,000 $m/s^2$, at least 60,000 $m/s^2$, at least 70,000 $m/s^2$, at least 80,000 $m/s^2$, at least 85,000 $m/s^2$, at least 90,000 $m/s^2$, at least 95,000 $m/s^2$, or at least 100,000 $m/s^2$). In some cases, a processor is configured to retract the insertion needle with an acceleration in a range of from 50,000 to 200,000 $m/s^2$ (e.g., from 50,000 to 150,000 $m/s^2$, from 50,000 to 125,000 $m/s^2$, from 50,000 to 115,000 $m/s^2$, from 50,000 to 100,000 $m/s^2$, from 60,000 to 200,000 $m/s^2$, from 60,000 to 150,000 $m/s^2$, from 60,000 to 125,000 $m/s^2$, from 60,000 to 115,000 $m/s^2$, from 60,000 to 100,000 $m/s^2$, from 70,000 to 200,000 $m/s^2$, from 70,000 to 150,000 $m/s^2$, from 70,000 to 125,000 $m/s^2$, from 70,000 to 115,000 $m/s^2$, from 70,000 to 100,000 $m/s^2$, from 80,000 to 200,000 $m/s^2$, from 80,000 to 150,000 $m/s^2$, from 80,000 to 125,000 $m/s^2$, from 80,000 to 115,000 $m/s^2$, from 80,000 to 100,000 $m/s^2$, from 90,000 to 200,000 $m/s^2$, from 90,000 to 150,000 $m/s^2$, from 90,000 to 125,000 $m/s^2$, from 90,000 to 115,000 $m/s^2$, or from 90,000 to 100,000 $m/s^2$).

In some cases, a processor is configured to retract the insertion needle with a speed of at least 0.4 meters per second (m/s) (e.g., at least 0.5 m/s, at least 0.6 m/s, at least 0.7 m/s, at least 0.8 m/s, at least 0.9 m/s, at least 1 m/s, at least 1.5 m/s, at least 2 m/s, or at least 2.5 m/s). In some cases, a processor is configured to retract the insertion needle with a speed in a range of from 0.4 to 3 m/s (e.g., from 0.4 to 2.5 m/s, from 0.4 to 2 m/s, from 0.4 to 1.5 m/s, from 0.4 to 1 m/s, from 0.5 to 3 m/s, from 0.5 to 2.5 m/s, from 0.5 to 2 m/s, from 0.5 to 1.5 m/s, from 0.5 to 1 m/s, from 0.6 to 3 m/s, from 0.6 to 2.5 m/s, from 0.6 to 2 m/s, from 0.6 to 1.5 m/s, from 0.6 to 1 m/s, from 0.7 to 3 m/s, from 0.7 to 2.5 m/s, from 0.7 to 2 m/s, from 0.7 to 1.5 m/s, from 0.7 to 1 m/s, from 0.8 to 3 m/s, from 0.8 to 2.5 m/s, from 0.8 to 2 m/s, from 0.8 to 1.5 m/s, from 0.8 to 1 m/s, from 0.9 to 3 m/s, from 0.9 to 2.5 m/s, from 0.9 to 2 m/s, from 0.9 to 1.5 m/s, from 0.9 to 1 m/s, from 1 to 3 m/s, from 1 to 2.5 m/s, from 1 to 2 m/s, or from 1 to 1.5 m/s).

In some cases, a processor can be configured to rotate the insertion needle about is longitudinal axis during insertion and/or retraction (e.g., as described elsewhere herein). For example, in some cases, a processor can be configured to rotate the insertion needle in one direction about its longitudinal axis during insertion, and in the opposite direction about its longitudinal axis during retraction.

Thus, in some cases, a subject system includes a computer system. The computer systems include a processor (e.g., or a plurality of processors) and memory operably coupled to a processor, where the memory can program a processor to perform tasks, e.g., those described above for the process (e.g., manipulating an insertion device and/or insertion needle into position over a target biological tissue, manipulating an insertion device and/or insertion needle toward an implantable device cartridge in order to engage an implantable device, insert or retract an insertion needle (e.g., into/out from a biological tissue, e.g., in some cases at particular and/or controlled speeds, in some cases to a particular depth in the tissue), rotate an insertion needle, e.g., during insertion and/or retraction, and the like).

Computer systems may include a processing system, which generally comprises at least one processor or processing unit or plurality of processors, memory, at least one input device and at least one output device, coupled together via a bus or group of buses. In certain embodiments, an input device and output device can be the same device. The memory can be any form of memory device, for example, volatile or non-volatile memory, solid state storage devices, magnetic devices, etc. In some cases, a processor can comprise more than one distinct processing device, for example to handle different functions within the processing system.

An input device receives input data and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data can come from different sources, for example keyboard instructions in conjunction with data received via a network.

Output devices produce or generate output data and can comprise, for example, a display device or monitor in which case output data is visual, a printer in which case output data is printed, a port for example a USB port, a peripheral component adaptor, a data transmitter or antenna such as a modem or wireless network adaptor, etc. Output data can be distinct and derived from different output devices, for example a visual display on a monitor in conjunction with data transmitted to a network. A user can view data output, or an interpretation of the data output, on, for example, a monitor or using a printer. The storage device can be any form of data or information storage means, for example, volatile or non-volatile memory, solid state storage devices, magnetic devices, etc.

In use, the processing system may be adapted to allow data or information to be stored in and/or retrieved from, via wired or wireless communication means, at least one database. The interface may allow wired and/or wireless communication between the processing unit and peripheral components that may serve a specialized purpose. In general, a processor can receive instructions as input data via input device and can display processed results or other output to a user by utilizing output device. More than one input device and/or output device can be provided. A processing system may be any suitable form of terminal, server, specialized hardware, or the like.

A processing system may be a part of a networked communications system. A processing system can connect to a network, for example the Internet or a WAN. Input data and output data can be communicated to other devices via the network. The transfer of information and/or data over the network can be achieved using wired communications means or wireless communications means. A server can facilitate the transfer of data between the network and one or more databases. A server and one or more databases provide an example of an information source.

Thus, a processing computing system environment may operate in a networked environment using logical connections to one or more remote computers. The remote computer may be a personal computer, a server, a router, a network PC, a peer device, or other common network node, and typically includes many or all of the elements described above.

Certain embodiments may be described with reference to acts and symbolic representations of operations that are performed by one or more computing devices. As such, it will be understood that such acts and operations, which are at times referred to as being computer-executed, include the manipulation by a processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

Utility

The methods, components, and systems provided herein can be transformative for understanding and treating the brain. For example: (i) roughly 10,000 of the present implantable device design can be inserted per 1 $cm^2$ of cortex with only 0.8% tissue displacement; (ii) each implantable device can be 20,000 times more flexible than an equivalent commonly-used stainless steel microwire or silicon shank; (iii) because a subject insertion needle can be laterally supported right to the point that it enters the brain, it can be much smaller than a conventional microwire equally able to penetrate; and (iv) the scale at which the components can be made facilitates the avoidance of blood vessels during insertion.

As noted above, a subject implantable device can be used for a large variety of purposes, and this will depend on the nature of the conduit(s) present as part of the implantable device. For example, an implantable device can be used as (1) a sensor (detector), (2) an effector (e.g., to deliver a stimulation such as light, current, and/or a drug, e.g., which can change the tissue environment into which the device is implanted), or (3) both, depending on the nature of the conduit(s) present as part of the implantable device.

Examples of when a subject implantable device can be used as a sensor include, but are not limited to situations in which the device includes, as a conduit: (i) an electrode that is used as a recording electrode; (ii) a chemical sensing element such as an analyte sensor, e.g., a working electrode; (iii) a photodetector, e.g., for radiography and/or in-vivo imaging; etc.

Examples of when a subject implantable device can be used as an effector include, but are not limited to situations in which the device includes, as a conduit: (i) an electrode that is used for stimulation, e.g., for delivering a current; (ii) a light emitting diode (LED) and/or a microscale laser, e.g., for optogenetic applications; and/or (iii) a waveguide (e.g., optical fiber) for delivering light, e.g., for optogenetic applications (e.g., where the implantable device includes a waveguide and a Nickel-Titanium (NiTi) loop, and the like); etc.

Thus, in addition to recording electrical tissue activity (e.g., recording brain activity), implanted implantable devices described herein can be used in any number of wide range of methods. Suitable applications include but are not limited to: embedding chemical sensing elements, like cyclic voltammetry, within subject implantable devices; embedding microscale LEDs or lasers on the implantable device for optogenetic applications; and embedding high-sensitivity photodetectors for radiography or in-vivo imaging of activity, and using implanted implantable devices having electrodes for deep brain stimulation.

The provided systems can revolutionize the field of neural interfaces, for both research and clinical purposes. The subject methods will allow multi-scale neural recording (e.g., from single spikes to local field potentials), combined with precisely controlled electrical stimulation, at 1000's of sites from across the brain. Furthermore, this system will achieve unparalleled levels of stability. The methods also scale to extremely broad sampling, interfacing with dozens of brain areas, e.g., completely covering the brain-wide circuits implicated in major depression or generalized anxiety disorder.

Example Embodiments

One illustrative embodiment of the subject methods, components, and systems is depicted in FIG. 1, in which a plurality of implantable devices 200 are being implanted into a biological tissue 10 (e.g., a brain as depicted). In the depicted embodiment, an insertion device 1 manipulates an insertion needle 100 to engage an implantable device 200 from a cartridge 500 that includes a plurality of implantable devices. The device-loaded insertion needle is inserted into the brain 10 to a desired depth (which, as depicted, can be independently determined for each implantable device 200 that is implanted). The insertion needle 100 is then retracted, thereby disengaging the implantable device 200 from the insertion needle 100 and allowing the implantable device 200 to remain implanted in the biological tissue 10. In the depicted embodiment, each implantable device 200 includes a conduit (e.g., an electrode, waveguide) that is in communication (e.g., electrical communication, optic communication) with an external device (not shown) via a wire or fiber 240.

Figure 3B:
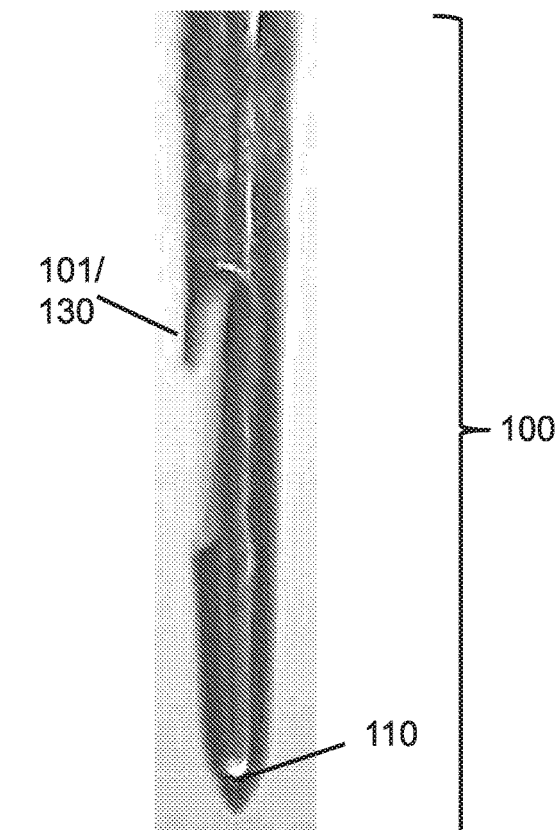
Figure 3C:
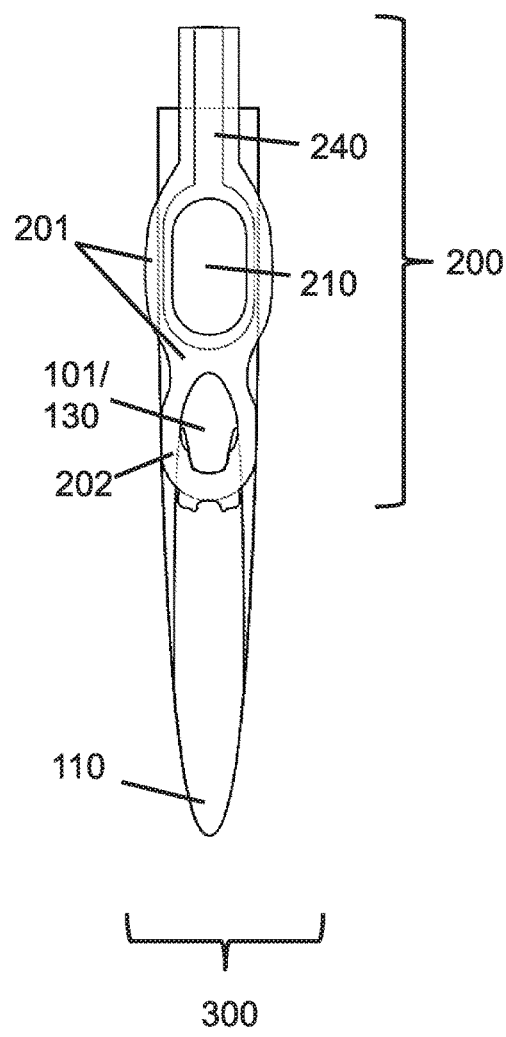
Figure 3D:
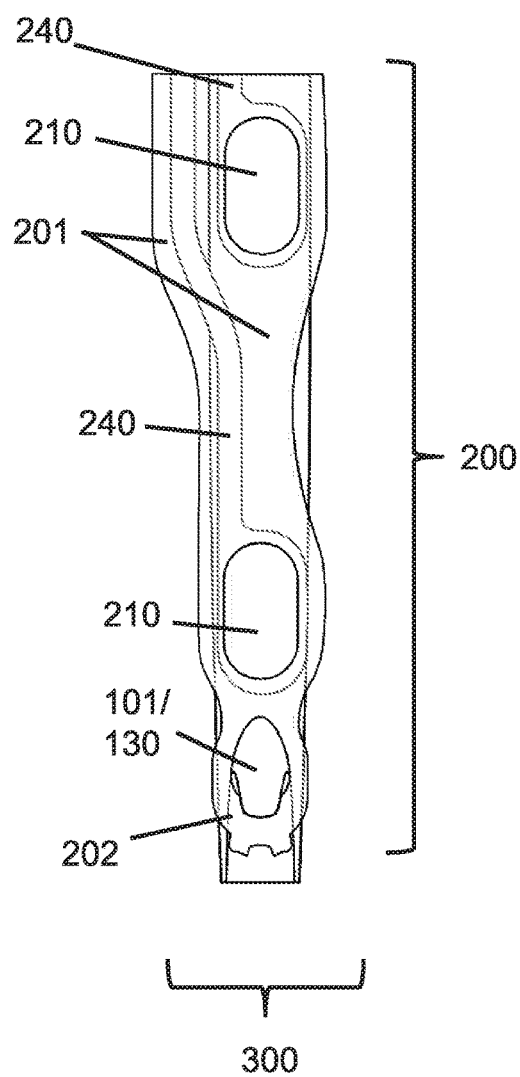
Figure 3E:
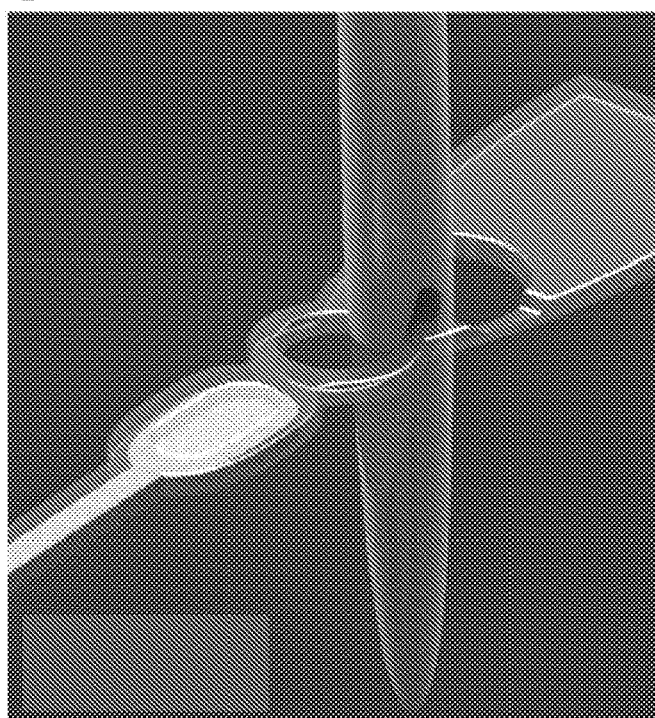

FIGS. 3A and 3C-3E each illustrate an embodiment in which an insertion needle 100 is reversibly engaged with an implantable device 200, forming a device-loaded insertion needle 300. The depicted implantable device includes (i) a biocompatible substrate 201 that includes an engagement feature 202 (a loop in this case) that corresponds to the engagement feature 101 of the depicted insertion needle 100; and (ii) a conduit 210 (e.g., an electrode, waveguide) that is disposed on the biocompatible substrate. In the depicted embodiments, the engagement feature 101 of the insertion needle 100 is a flange formed from a notch carved into the body of the insertion needle that penetrates 130 through the loop (the engagement feature 202) of the implantable device 200. In the depicted embodiments, the conduit 210 (e.g., an electrode, waveguide) is in communication (e.g., electrical communication, optic communication) with an external device via a wire or fiber 240. In some cases, an implantable device 200 is implanted prior to putting the conduit 210 into communication (e.g., electrical communication, optic communication) with an external device (e.g., prior to connecting the wire or fiber 240 to an external device). In some cases, the conduit 210 is in communication (e.g., electrical communication, optic communication) with an external device prior to implanting the implantable device 200 (e.g., the wire or fiber 240 is connected to an external device prior to implantation of the implantable device 200). In the embodiment depicted in FIG. 3D, the implantable device 200 includes two conduits 210 (e.g., two electrodes, two waveguides) that are each in communication (e.g., electrical communication, optic communication) with an external device via respective wires or fibers 240. Also depicted (but not shown in FIG. 3D) is the distal end 110 of the insertion needle 100 of the device-loaded insertion needle 300. FIG. 3B is a photograph of an insertion needle 100 (as depicted in FIG. 3A and FIG. 3C-3E) that includes a notch (e.g., carved into the body of the insertion needle) as the engagement feature 101 of the insertion needle 100. Also depicted in FIG. 3B is the distal end 110 of the insertion needle 100. FIG. 3E depicts an insertion needle 100 engaging an implantable device 200 in which the implantable device is attached to a break-away tab. FIG. 3A and FIG. 3B: side view. FIG. 3C and FIG. 3D: front View. FIG. 3E: angled view.

Figure 4A:
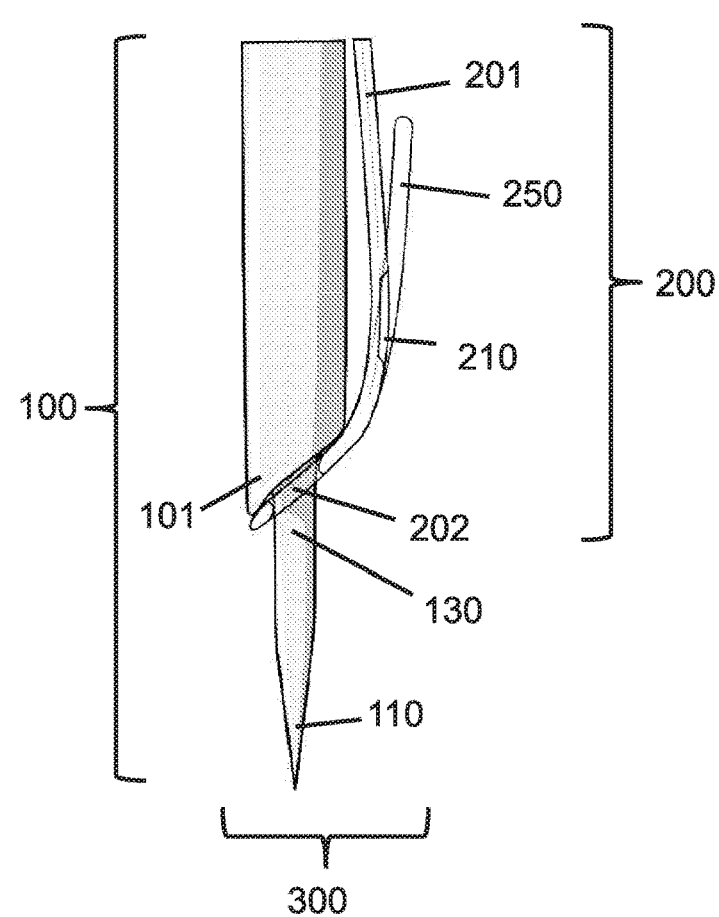
FIG. 4A-4B depict embodiments in which an insertion needle includes an engagement feature that is a flange formed from a step in the diameter of the insertion needle.
Figure 4B:
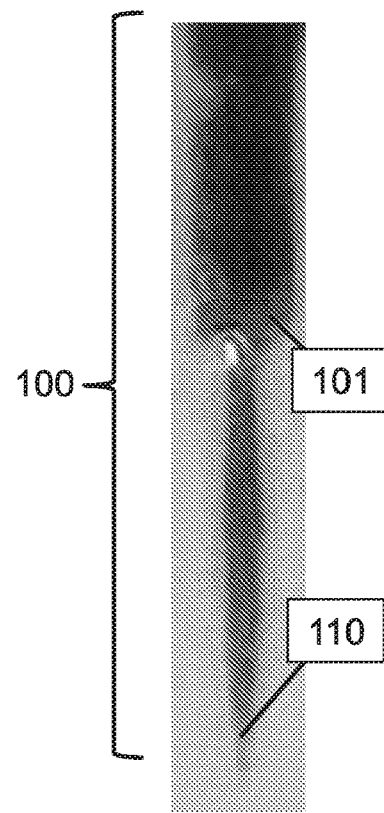
Figure 5A:
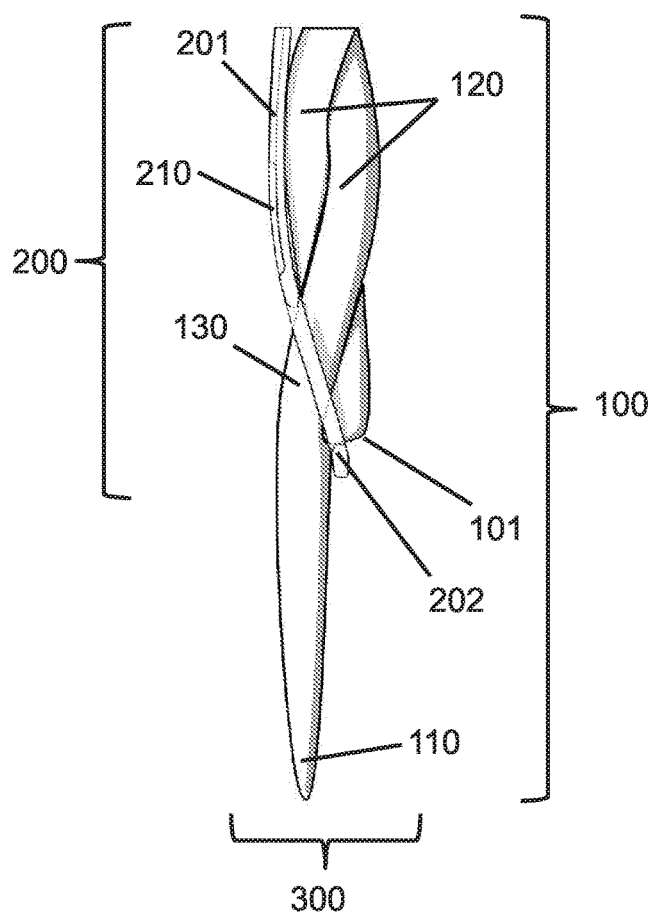
FIG. 5A-5D depict embodiments in which an insertion needle includes an engagement feature that is a flange formed from two wires twisted together forming a helix, where one of the two wires is shorter than the other such that the distal end of the shorter wire forms the flange.

FIG. 4A illustrates an embodiment in which an insertion needle 100 is reversibly engaged with an implantable device 200, forming a device-loaded insertion needle 300. The depicted implantable device includes (i) a biocompatible substrate 201 that includes an engagement feature 202 (a loop in this case) that corresponds to the engagement feature 101 of the depicted insertion needle 100; and (ii) a conduit 210 (e.g., an electrode, waveguide) that is disposed on the biocompatible substrate. Also in the depicted embodiment, the biocompatible substrate 201 of the implantable device 200 includes an anchor arm 250 configured to flex orthogonal to the body of the implantable device, while remaining connected to the implantable device (e.g., in order to facilitate anchoring of the implantable device in the biological tissue upon retraction of the insertion needle 100). The anchor arm 250 can be configured such that the flex of the anchor arm orthogonal to the body of the implantable device distorts the engagement feature 202 of the implantable device 200, which can facilitate disengagement of the implantable device 200 from the insertion needle 100. In the depicted embodiment, the engagement feature 101 of the insertion needle 100 is a flange 101 formed from a step in the diameter of the insertion needle 100. Also in the depicted embodiment, the insertion needle 100 penetrates 130 through the loop (the engagement feature 202) of the implantable device 200. Also depicted is the distal end 110 of the insertion needle 100 of the device-loaded insertion needle 300. FIG. 4B is a photograph of an insertion needle 100 that includes a flange 101 formed from a step in the diameter of the insertion needle 100. Also depicted in FIG. 4B is the distal end 110 of the insertion needle 100. FIG. 4A: side view.

Figure 5B:
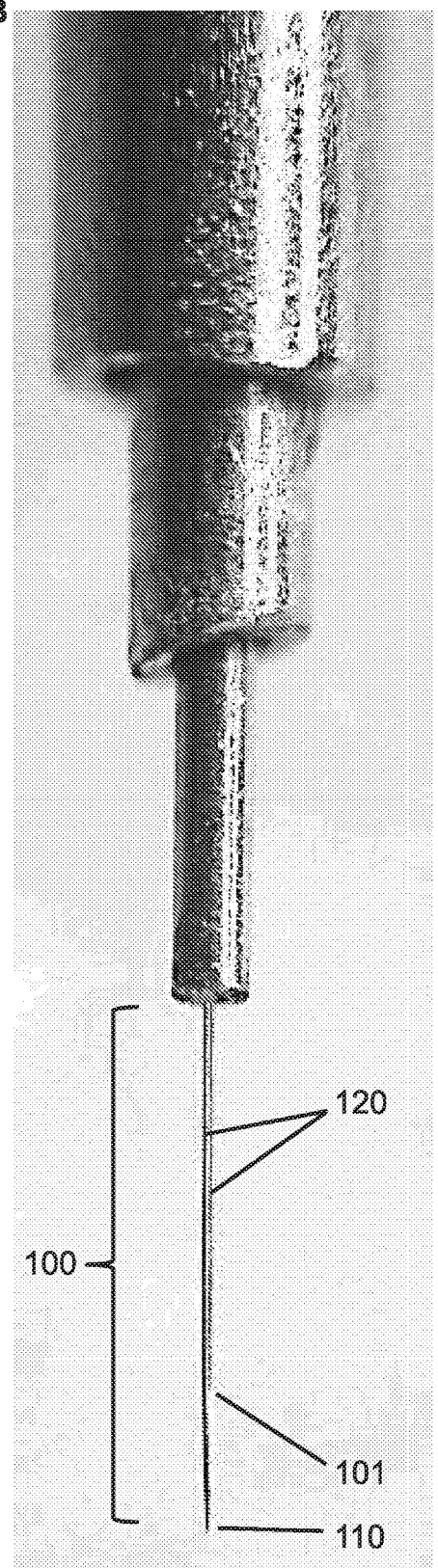
Figure 5C:
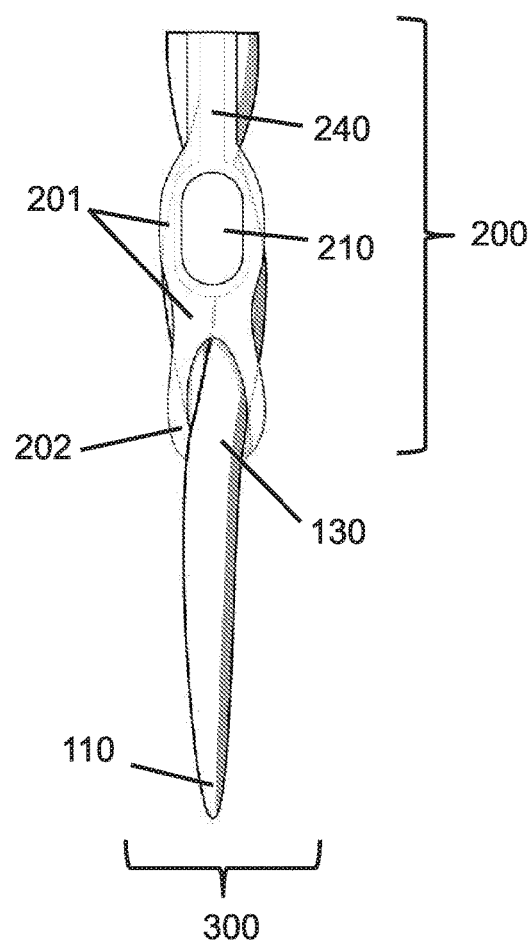
Figure 5D:
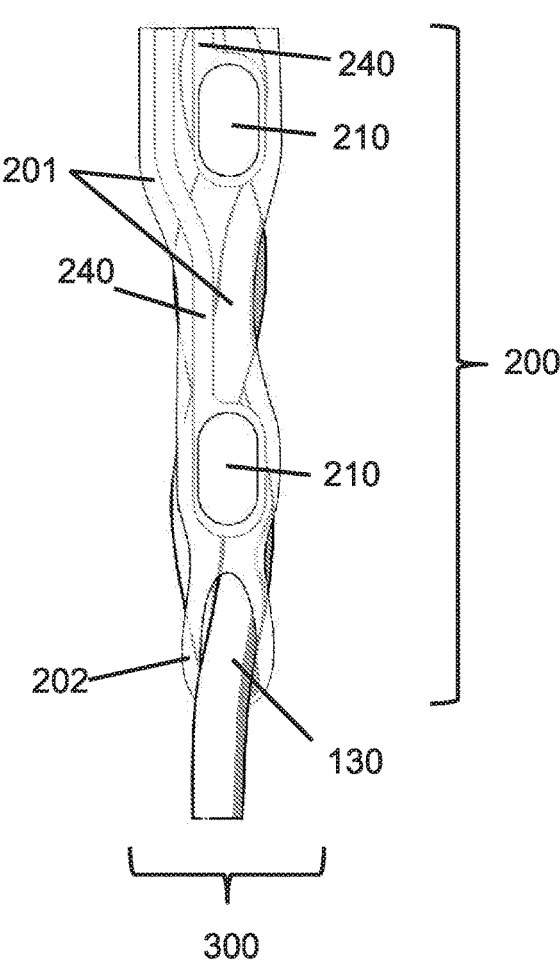

FIGS. 5A and 5C-5D each illustrate an embodiment in which an insertion needle 100 is reversibly engaged with an implantable device 200, forming a device-loaded insertion needle 300. The depicted implantable device includes (i) a biocompatible substrate 201 that includes an engagement feature 202 (a loop in this case) that corresponds to the engagement feature 101 of the depicted insertion needle 100; and (ii) a conduit 210 (e.g., an electrode, waveguide) that is disposed on the biocompatible substrate. In the depicted embodiments, the engagement feature 101 of the insertion needle 100 is a flange 101 formed from two wires 120 twisted together forming a helix, where one of the two wires is shorter than the other such that the distal end of the shorter wire forms the flange 101. In the depicted embodiments, the insertion needle 100 penetrates 130 through the loop (the engagement feature 202) of the implantable device 200. In the depicted embodiments, the conduit 210 (e.g., an electrode, waveguide) is in communication (e.g., electrical communication, optic communication) with an external device via a wire or fiber 240. In some cases, an implantable device 200 is implanted prior to putting the conduit 210 into communication (e.g., electrical communication, optic communication) with an external device (e.g., prior to connecting the wire or fiber 240 to an external device). In some cases, the conduit 210 is in communication (e.g., electrical communication, optic communication) with an external device prior to implanting the implantable device 200 (e.g., the wire or fiber 240 is connected to an external device prior to implantation of the implantable device 200). In the embodiment depicted in FIG. 5D, the implantable device 200 includes two conduits 210 (e.g., two electrodes) that are each in communication (e.g., electrical communication, optic communication) with an external device via respective wires or fibers 240. Also depicted (but not shown in FIG. 5D) is the distal end 110 of the insertion needle 100 of the device-loaded insertion needle 300. FIG. 5B is a photograph of an insertion needle 100 that includes a flange 101 formed from two connected wires 120 where one of the two wires is shorter than the other such that the distal end of the shorter wire forms the flange 101. Also depicted in FIG. 5B is the distal end 110 of the insertion needle 100. FIG. 5A and FIG. 5B: side view. FIG. 5C and FIG. 5D: front View.

Figure 6A:
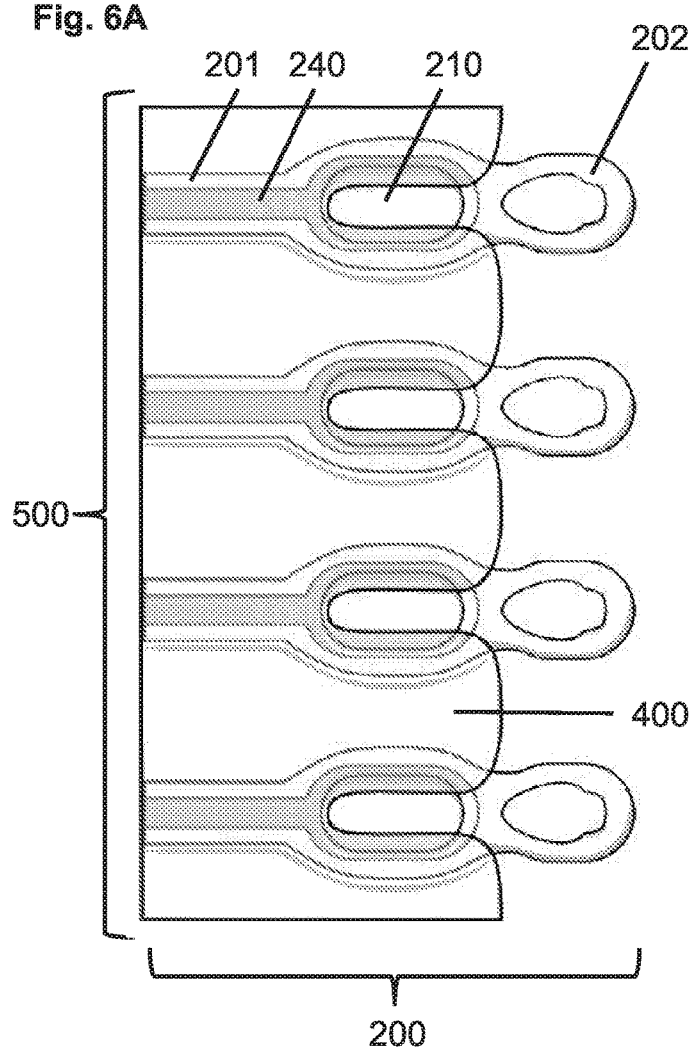
FIG. 6A-6C depict an implantable device cartridge (a cartridge that includes a plurality of implantable devices). The depicted cartridges include a flexible backing sheet (e.g., a parylene film) to which the implantable devices adhere.
Figure 6B:
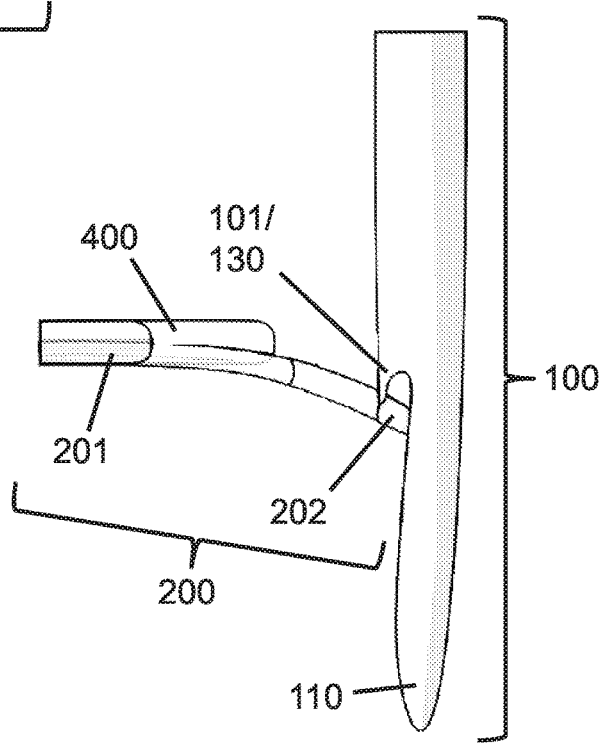
Figure 6C:
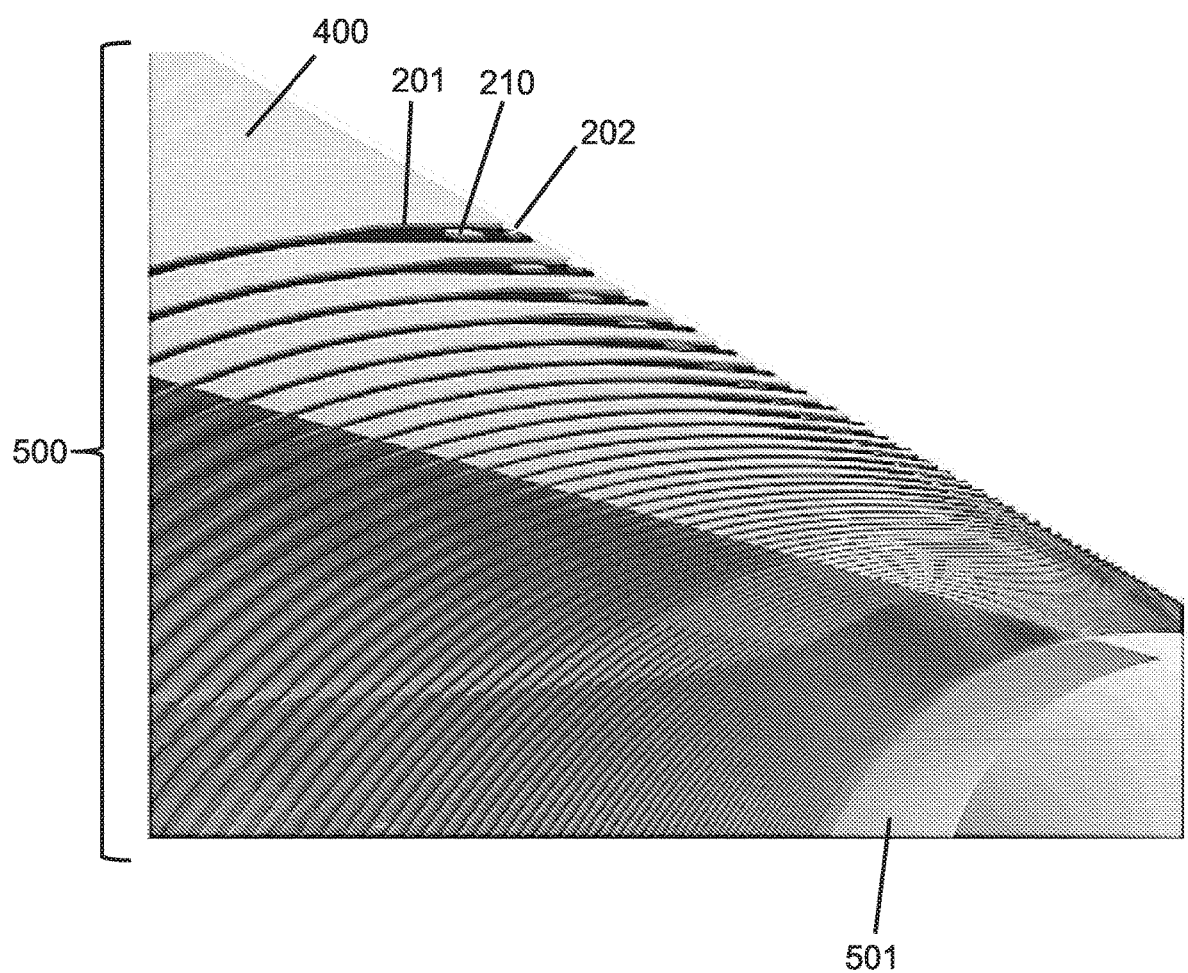

FIG. 6A-6C illustrate a cartridge 500 that includes a plurality of subject implantable devices 200. The depicted cartridges 500 include a flexible backing sheet 400 (e.g., a parylene film) to which the plurality of implantable devices is adhered. In some such cases, each implantable device 200 can be removed from the cartridge 500 by engaging the engagement feature 202 of the implantable device 200 with a corresponding engagement feature 101 of an insertion needle 100 and delaminating the engaged implantable device from the flexible backing sheet 400. In some cases, a cartridge 500 includes a solid support 501 to provide support for the flexible backing sheet 400. The implantable devices 200 each include (i) a biocompatible substrate 201 that include an engagement feature 202 (in this case a loop) configured for reversible engagement with a corresponding engagement feature 101 of an insertion needle 100; and (ii) a conduit 210 (e.g., an electrode, waveguide) disposed on the biocompatible substrate 201. In the depicted embodiments, the conduit 210 (e.g., an electrode, waveguide) is in communication (e.g., electrical communication, optic communication) with an external device (not shown) via a wire or fiber 240. In some cases, an implantable device 200 is implanted prior to putting the conduit 210 into communication (e.g., electrical communication, optic communication) with an external device (e.g., prior to connecting the wire or fiber 240 to an external device). In some cases, the conduit 210 is in electrical communication with an external device prior to implanting the implantable device 200 (e.g., the wire or fiber 240 is connected to an external device prior to implantation of the implantable device 200). When engaged, the engagement feature 101 of the insertion needle 100 depicted in FIG. 6B protrudes 130 through the engagement feature 202 of the implantable device 200.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1

FIG. 9A-9F show photographs (successful working examples) of a subject system performing a subject method (e.g., in this case inserting a plurality of implantable devices into agar as a substitute for a biological tissue). The shown system includes an insertion device 1 that includes a brake 600 and a cannula 700 (through which an insertion needle is extended). Also shown is a cartridge 500 of implantable devices, where the cartridge includes: (i) a flexible backing sheet (made of parylene) to which a plurality of implantable devices is adhered, and (ii) a solid support 501 for the flexible backing sheet. Shown in FIG. 9E is a device-loaded insertion needle 300 extending through the cannula 700 out from the insertion device 1 to implant an implantable device (in this case the implantable device includes an electrode connected to a wire 240). The brake 600 in FIG. 9A-9F was used to prevent the wire 240 from laterally slicing into the target tissue (agar in this case). FIG. 9F shows the brake 600 swinging out of the way once the implantable device has been implanted.

Shown in FIG. 9B, under microscope guidance, the insertion needle was positioned through the engagement feature (a loop in this case) of one implantable device of the implantable device cartridge 500. The Brake 600 was moved to clamp the implantable device loosely against the cannula 700. Shown in FIG. 9C, the insertion needle was moved to peel (delaminate) the engaged implantable device off of the flexible backing sheet (parylene in this case). Shown in FIG. 9D, The device-loaded insertion needle was positioned above the desired insertion site. Shown in FIG. 9E, the device-loaded insertion needle 300 was advanced (extended), and as it was advanced it was rotated about its longitudinal axis. As device-loaded insertion needle 300 was advance, it was also rotated, spiraling the implantable device and attached wire 240 slightly around it as it entered the target tissue. Shown in FIG. 9E, the insertion needled was retracted, the brake was swung out of the way, and the insertion needle was free to engage another implantable device and continue the cycle. As the insertion needle was retracted (disengaging from the implanted implantable device), it was rotated about its longitudinal axis in the opposite direction as during insertion, so that the spiral formed during insertion (e.g., of the wire 240 around the insertion needle) was unwrapped, enabling release from the insertion needle.

FIG. 10A-10E show photographs (successful working examples) of implantable devices (having electrodes, each connected to a respective wire) that were successfully implanted using a subject system. FIG. 10A-10B demonstrate successful implantation of a plurality of implantable devices into agar (as a substitute for a biological tissue). FIG. 10A is a picture demonstrating successful implantation of twenty implantable devices (each of which includes an electrode and a connected wire) at 500 μm spacing in two rows into 0.6% w/v agar (as an illustrative substitute for a biological tissue). FIG. 10B is a picture demonstrating successful implantation of ten implantable devices (each of which includes an electrode and a connected wire) 200 μm spacing into agar (as an illustrative substitute for a biological tissue). Top: view of implanted implantable devices in agar. Bottom: view of wires outside of the agar that connect to the implanted implantable devices. FIG. 10C is a picture of three implantable devices (each of which includes an electrode and a connected wire) successfully implanted into a zebra finch brain (ex vivo). FIG. 10D is a picture of seven implantable devices (each of which includes an electrode and a connected wire) successfully implanted into the opposite hemisphere of the brain shown in FIG. 10O. FIG. 10F is a picture of four implantable devices (each of which includes an electrode and a connected wire) successfully implanted into a rat brain.

Example 2

As noted above, FIG. 8A-8C depict illustrative examples of methods to fabricate a subject implantable device (i.e., implantable device fabrication), in this case a plurality of implantable devices are fabricated as a cartridge that includes a flexible backing sheet comprising parylene. FIG. 8A depicts the first nine steps that were used to generate the implantable devices (as depicted in FIG. 8B-8C). For example, two different illustrative example methods are presented, the first nine steps for both example methods are presented in FIG. 8A, and the remaining steps (steps ten to sixteen) of example method 1 are presented in FIG. 8B, while the remaining steps (steps ten to fifteen) of example method 2 are presented in FIG. 8C. For both presented example methods, the implantable devices were produced via etching (e.g., dry and/or wet etching).

FIG. 8A. Step 1: 1.5-2 µm polyimide was spun onto a clean silicon wafer from the precursor, polyamic acid. The thin layer of native $SiO_2$ provided a controlled level of adhesion to the substrate (e.g., high enough that the film remained on during fabrication steps, but low enough that it could be released at the end of the process). Step 2: Polyimide (PI) was cured at 250°-300° C. for 30 minutes. This was enough to imidize the film and drive off the solvent (NMP in this case), but not enough to fully order the molecular chains. Step 3: Lift-off resist was spun and patterned, and either a metal stack of (i) SiC—Ti—Pt—SiC [SiC (used as an adhesion layer, sputtered, 30 nm) Ti (e-beam, 10 nm) Pt (e-beam, 80 nm) SiC (used as an adhesion layer, sputtered, 30 nm)], or, or (ii) Cr—Au [Cr (e-beam, 30 nm) Au (e-beam 100 nm)] was applied. For the SiC—Ti—Pt—SiC metalization stack, SiC showed high adhesion to polyimide while Ti served as the adhesion layer between Pt and SiC. Step 4: A second layer of PI was spun over the conductors and first polyimide layer. Step 5: This layer was cured at 450° C. for 30 min in the case of SiC—Ti—Pt—SiC to promote PI— SiC adhesion, and to promote the formation of PtSi and adhesion of SiC to Pt. By raising the polymer above its glass transition temperature, this also increased the adhesion of PI to PI (second layer adhesion to first layer). Step 6: Greater than 200 nm of $SiO_2$ was applied via plasma-enchanced chemical-vapor deposition. The silicon dioxide served as both a hardmask for subsequent oxygen plasma etch steps, and as a release layer for the parylene, which was applied later. Step 7: Surface was primed, photoresist (PR) was applied, patterned, ultraviolet (UV) baked, and $SiO_2$ was etched in a $CF_4/CHF_3$ plasma, delineating the outlines of the implantable devices. Step 8: PI was etched, and photoresist ashed, in an oxygen plasma, forming the outside geometry of the implantable devices. Step 9: Surface was primed again, PR spun/patterned, and SiC was etched in a $SF_6/O_2$ plasma. The PR served to protect the $SiO_2$ hardmask and underlying silicon from being etched.

FIG. 8B. Step 10 (following step 9 of FIG. 8A): 400-800 nm of Cu was deposited (e-beam), and patterned via photoresist and etching in $FeCl_3$. Step 11: The copper formed current busses for electroplating 5-15 µm nickel on the bondpads. Step 12: PR was spun and patterned to protect the Ni bondpads. Without this, parylene can stick to the nickel. Step 13: 3 µm of parylene was vacuum deposited (Gorham process) onto the wafers. Step 14: An aluminum hardmask (via thermnal or e-beam) was evaporated over the the parylene, and patterned via PR & wet etched. Step 15: Oxygen plasma etched the outlines of the parylene backing sheet. Step 16: Implantable devices (that each include an electrode) were lifted off the wafer in warm water, bonded using a phenol-novolak thermoset epoxy to printed circuit boards (PCBs), and wire bonded to the external traces.

FIG. 8C. Step 10 (following step 9 of FIG. 8A): 3-5 µm of parylene was vacuum deposited (Gorham process) onto the wafers. Step 11: An aluminum hardmask was evaporated over the parylene. Step 12: The hardmask was patterned via PR & wet etched. Step 13: Oxygen plasma etched the outlines of the parylene backing sheet. Step 14: Implantable devices were removed from the wafer in warm water, and epoxy bonded to a printed circuit board (PCB). A UV laser (e.g., 405 nm) was used to drill micro-vias in the PI and epoxy. Step 15: Nickel was electroplated to fill the vias and bond the electrode conductors to the underlying PCB. These nickel plated vias could then be ultrasonically wire bonded e.g. to an IC.

Example 3

As noted above, this example provides a description of example protocols that were used to produce three different types of insertion needles, e.g., one with a flange formed from a notch carved into the body of the needle, one with a flange formed from a step in the diameter of the insertion needle, and one with a flange formed from two wires twisted together forming a helix, where one of the two wires is shorter than the other such that the distal end of the shorter wire forms the flange.

Three different protocols are described here that were used to produce the insertion needles depicted in FIG. 3A-3E, FIG. 4A-4B, FIG. 5A-5D. Two additional example protocols are also provided: continuous-melt copper brazing, and dicing-saw notch cutting.

Notch

For an insertion needle with a flange formed from a notch carved into the body of the needle (as the engagement feature) (e.g., see FIG. 3A-3E), conventional laser micromachining methodology was employed to add the notch into a 50 µm (diameter) tungsten wire.

Radial Step

For an insertion needle with a flange formed from a step in the diameter of the insertion needle (i.e., a radial step)(as the engagement feature) (e.g., see FIG. 4A-4B), a carefully-applied nail polish was used as an etch mask, modified to a ball by passing over acetone vapors. A sharp radial step was etched into a 25 µm needle. Tungsten was etched in 0.5 M NaOH solution at +4V.

Helical Twist (Micro-Brazing)

For an insertion needle with a flange formed from two wires twisted together forming a helix, where one of the two wires is shorter than the other such that the distal end of the shorter wire forms the flange (as the engagement feature) (e.g., see FIG. 5A-5D), a gold micro-brazed twisted triple needle was produced (see FIG. 11A for a picture of the laser micro-brazing machine that was used): Step 1: Three wires were installed in the brazing machine jig: two 12 µm tungsten wires and one 25 µm tungsten wire. The 25 µm wire did not enter the biological tissue, but instead was used to prevent buckling during retraction of the insertion needle (e.g., during ballistic retraction), within the telescoping region of the needle cartridge (an insertion device), and also permitted manual loading into the needle cartridge (an insertion device); Step 2: The jig was installed in the machine, and it was pumped down to −20 mTorr; Step 3: Wires were heated to ~1500° C. in a low-pressure oxygen-containing (residual $N_2/O_2$ atmosphere) environment to oxidize surface tungsten carbide left from the wire drawing process. Wires were heated with two current-controlled 3.5 W 445 nm diode lasers mounted orthogonal to the axis of the wire. Lasers were scanned with a low-speed motor; Step 4: An argon/hydrogen mix (e.g., 95:5%) was back filled and flowed to ~1 Torr, and the wires were heated again, reducing the tungsten oxide to tungsten; Step 5: The jig was removed, and a 25 μm gold wire was wrapped around the 12/12/25 μm wire bundle; Step 6: The jig was re-installed in the chamber, which was then pumped down and back filled with Ar/H$_2$. The gold wire was melted with the lasers to 17 mm from the end; Step 7: The jig was removed from the chamber, and the 25 μm wire was cut with either a Q-switched Nd:YAG 1064 nm laser, or with tungsten carbide cutters. More gold wire was wrapped around the twisted pair, if necessary; Step 8: Back in the Ar/H$_2$ chamber, lasers were then used to braze the 17 mm long 12 μm pair section, stopping a few mm from the end of the jig; Step 9: As with the 25 μm wire, one 12 μm wire was then cut with the Nd:YAG laser or carbide cutters. A small knot was tied with 25 μm gold wire around this cut (which formed the step for pushing in electrodes), and this was again brazed using the lasers in the vacuum chamber; Step 10: The lasers were run at near-full power and slightly lower Ar/H$_2$ pressure to evaporate away beads that formed due to volume of Au, which from the 25 μm wire is an excess of that needed to form a good braze fillet in the 12 μm twisted pair (and, to a lesser degree, the 12/12/25 triple); Step 11: The nascent needle was removed from the fabrication jig, inserted into the needle cartridge (itself composed of a telescoping group of successively larger hypodermic tubing), and installed into an insertion machine; Step 12: The longer end of the needle was sharpened/cut to length using the same NaOH anodic etching recipe as used above for the radial step insertion needle.

Figure 11A:
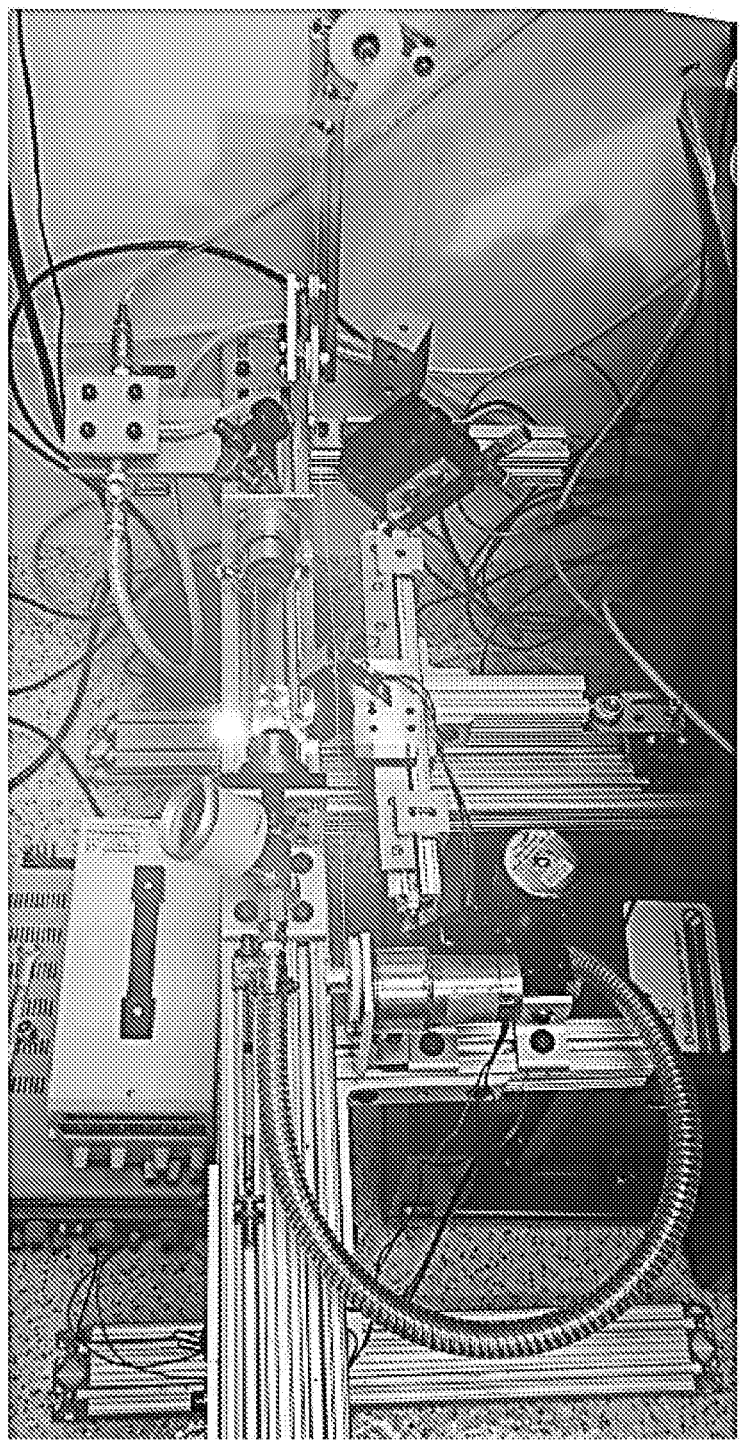
FIG. 11A-11B are pictures from various stages of examples of insertion needle fabrication (e.g., see example 3 of the experimental section).

FIG. 11A. View of the laser micro-brazing machine. Glass chamber, center near laser spot, holds the wires and assembly jig; linear slide to the right guides laser focal point laterally along the wires. Vacuum pump, bottom right; Ar/H$_2$ input gas manifold, upper left.

Continuous-Melt Copper Brazing

Tungsten wires were run through a continuous melt of copper or gold; as they were run through, the dross went into solution, surface tension limited the braze fillet to the correct volume, thereby eliminating beading, and the wire could then be heated resistively to oxidize/reduce surface contamination, or could be cleaned with an argon plasma. The machine can also be used to evaporate relatively thick films of copper onto the tungsten wires, which can make a step via standard lithography/etching. Finally, the same machine can be used to apply an adherent copper metalization to the tungsten; using low-temperature low-copper solubility solder alloys (e.g., silver-indium type), the wires may then be directly soldered in ambient without the additional difficulty of a reducing atmosphere.

Dicing-Saw Notch Cutting

Figure 11B:
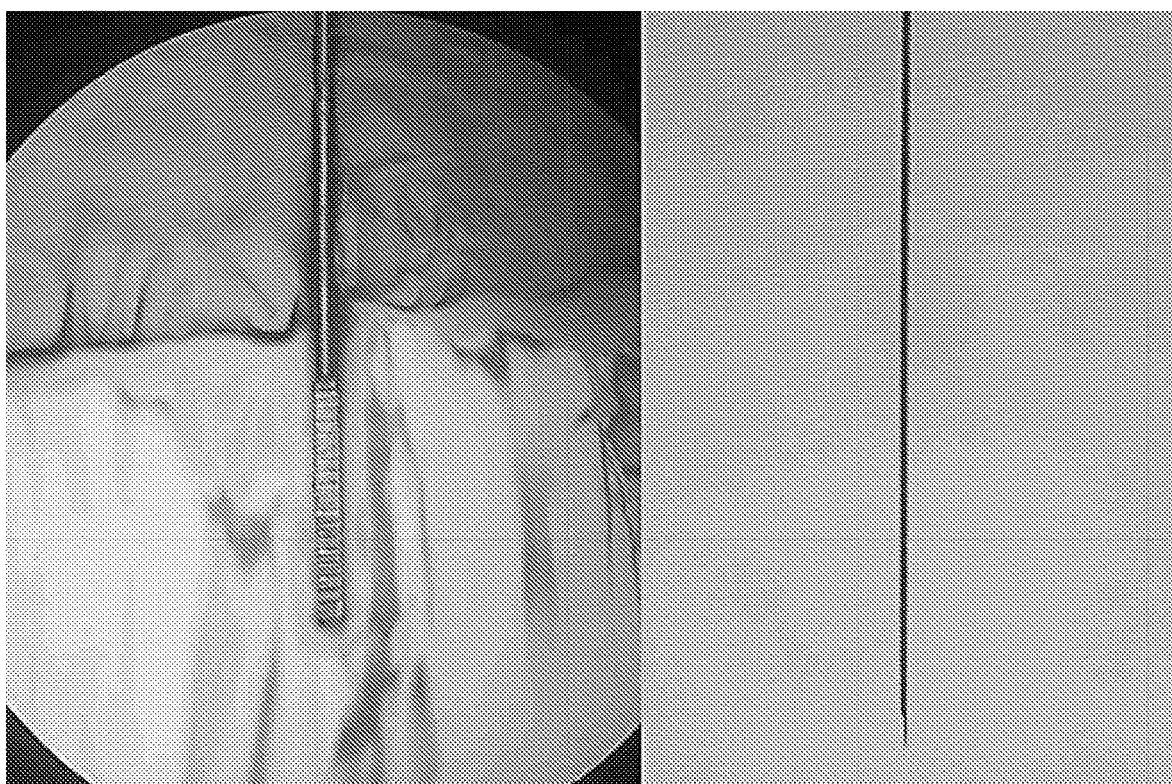

A wafer dicing saw was used to mill a step in 25 μm wires. The wires were wrapped around a double-flat 6 silicon wafer with thick (SPR-220) photoresist, which was baked at a low temperature (60 C) to minimize cracking. Excess wire is removed from the backside, the wafer was mounted in the dicing machine, and several experimental cuts were made to measure the top edge of the tungsten wires. Then sequential passes of the dicing saw cut slightly less than half way through the wire; these passes were staggered by 30 μm for a 45 μm kerf dicing saw. A final pass cut clean through the tungsten wires, which were then freed from the silicon wafer with acetone. These needles were installed, like the others, in a needle cartridge, and etched to a fine point anodically, as with the others described above. FIG. 11B shows an example.

FIG. 11B. Left, view of a 25 μm needle after milling with the dicing saw. Photoresist, brown, has been removed to show the wire more clearly; kerf cuts from multiple passes are clearly visible. Right, side view of this same needle after anodic etching.

That which is claimed is:

1. A system for implanting an implantable device, comprising:
   (a) an implantable device comprising:
      a biocompatible substrate;
      a conduit embedded in the biocompatible substrate; and
      an engagement feature that is: (i) fabricated within the biocompatible substrate at or near an end of the implantable device, and (ii) configured for reversible engagement with a corresponding engagement feature of an insertion needle; and
   (b) an insertion needle comprising an engagement feature that: (i) is a static protrusion on an external surface of the insertion needle, and (ii) corresponds to, and is configured to reversibly engage, the engagement feature of the implantable device.

2. The system of claim 1, wherein the conduit is a conductor of electrons and is an electrode for stimulating or recording.

3. The system of claim 1, wherein the conduit is a waveguide.

4. The system of claim 1, wherein the implantable device comprises two or more conduits.

5. The system of claim 4, wherein the two or more conduits include two or more electrodes.

6. The system of claim 1, wherein the biocompatible substrate comprises the engagement feature of the implantable device.

7. The system of claim 1, wherein the engagement feature of the implantable device is a loop.

8. The system of claim 1, wherein the biocompatible substrate of the implantable device is a non-conductive substrate.

9. The system of claim 1, wherein the biocompatible substrate of the implantable device comprises an inert polymeric material.

10. The system of claim 1, wherein the biocompatible substrate of the implantable device comprises polyimide.

11. The system of claim 1, wherein the biocompatible substrate of the implantable device includes one or more anchor arms configured to flex orthogonal to the body of the implantable device, while remaining connected to the implantable device, in order to facilitate anchoring of the implantable device.

12. The system of claim 1, wherein the implantable device is a member of a cartridge comprising a plurality of the implantable devices.

13. The system of claim 1, wherein the engagement feature of the insertion needle is positioned in a distal region of the insertion needle.

14. The system of claim 1, wherein the engagement feature of the insertion needle is positioned within 100 μm of the distal end of the insertion needle.

15. The system of claim 1, wherein the insertion needle has a maximum cross sectional area of 4000 μm$^2$ or less.

16. The system of claim 1, wherein the engagement feature of the insertion needle is a flange.

17. The system of claim 16, wherein the insertion needle comprises two connected wires and one of the two wires is shorter than the other such that the distal end of the shorter wire forms the flange.

18. The system of claim 16, wherein the flange is a notch or a ledge.

19. The system of claim 1, wherein the engagement feature of the insertion needle is reversibly engaged with the engagement feature of the implantable device.

20. The system of claim 19, wherein the insertion needle is configured to penetrate through the engagement feature of the implantable device.

\* \* \* \* \*

UNITED STATES PATENT AND TRADEMARK OFFICE
CERTIFICATE OF CORRECTION

PATENT NO. : 11,963,697 B2
APPLICATION NO. : 18/138978
DATED : April 23, 2024
INVENTOR(S) : Timothy L. Hanson et al.

It is certified that error appears in the above-identified patent and that said Letters Patent is hereby corrected as shown below:

In the Specification

In Column 3, Line 1, delete "is are" and insert -- is --.

In Column 13, Line 32, delete "to 35 µm." and insert -- 25 to 35 µm. --.

In Column 18, Line 24, delete "at least µm," and insert -- at least 40 µm, --.

In Column 18, Line 35, delete "at least µm," and insert -- at least 20 µm, --.

In Column 20, Line 21, after "from" insert -- 25 --.

In Column 24, Line 5, after "125,000 m/s$^2$" insert -- , --.

In Column 24, Line 7, after "200,000 m/s$^2$" insert -- , --.

In Column 24, Line 8, after "115,000 m/s$^2$" insert -- , --.

In Column 24, Line 10, after "150,000 m/s$^2$" insert -- , --.

In Column 24, Line 11, after "100,000 m/s$^2$" insert -- , --.

In Column 24, Line 13, after "125,000 m/s$^2$" insert -- , --.

In Column 24, Line 14, after "200,000 m/s$^2$" insert -- , --.

In Column 24, Line 16, after "200,000 m/s$^2$" insert -- , --.

In Column 25, Line 20, delete "FIG.100." and insert -- Fig. 10C. --.

Signed and Sealed this
Seventeenth Day of September, 2024

Katherine Kelly Vidal
*Director of the United States Patent and Trademark Office*

CERTIFICATE OF CORRECTION (continued)
U.S. Pat. No. 11,963,697 B2

In Column 26, Line 53, delete "FIG.100." and insert -- Fig. 10C. --.

In Column 34, Line 57, delete "FIG.100." and insert -- Fig. 10C. --.

In Column 35, Line 37, delete "plasma-enchanced" and insert -- plasma-enhanced --.

In Column 35, Line 56, delete "3 μm" and insert -- 3 - 5 μm --.

In Column 35, Line 57, delete "thernmal" and insert -- thermal --.

In Column 35, Line 57, delete "the the" and insert -- the --.